United States Patent
Bleck et al.

(10) Patent No.: US 12,157,897 B2
(45) Date of Patent: Dec. 3, 2024

(54) VECTORS FOR PROTEIN MANUFACTURE

(71) Applicant: CATALENT PHARMA SOLUTIONS, LLC, Somerset, NJ (US)

(72) Inventors: Gregory T. Bleck, Cross Plains, WI (US); Rachel H. Kravitz, Madison, WI (US); Chad A. Hall, Black Earth, WI (US)

(73) Assignee: CATALENT PHARMA SOLUTIONS, LLC, Somerset, NJ (US)

( * ) Notice: Subject to any disclaimer, the term of this patent is extended or adjusted under 35 U.S.C. 154(b) by 776 days.

(21) Appl. No.: 17/299,542

(22) PCT Filed: Dec. 4, 2019

(86) PCT No.: PCT/US2019/064423
§ 371 (c)(1),
(2) Date: Jun. 3, 2021

(87) PCT Pub. No.: WO2020/117910
PCT Pub. Date: Jun. 11, 2020

(65) Prior Publication Data
US 2022/0056476 A1 Feb. 24, 2022

Related U.S. Application Data

(60) Provisional application No. 62/775,194, filed on Dec. 4, 2018.

(51) Int. Cl.
*C12N 15/86* (2006.01)
*C07H 21/02* (2006.01)
*C07H 21/04* (2006.01)

(52) U.S. Cl.
CPC ............. *C12N 15/86* (2013.01); *C07H 21/02* (2013.01); *C07H 21/04* (2013.01); *C12N 2740/10043* (2013.01)

(58) Field of Classification Search
CPC .......... C12N 15/86; C12N 2740/10043; C07H 21/02; C07H 21/04
See application file for complete search history.

(56) References Cited

U.S. PATENT DOCUMENTS

| | | |
|---|---|---|
| 4,399,216 A | 8/1983 | Axel et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,139,941 A | 8/1992 | Muzyczka et al. |
| 5,149,636 A | 9/1992 | Axel et al. |
| 5,173,414 A | 12/1992 | Lebkowski et al. |
| 5,225,347 A | 7/1993 | Goldberg et al. |
| 5,512,421 A | 4/1996 | Burns et al. |
| 5,686,120 A | 11/1997 | Mertz et al. |
| 5,716,803 A * | 2/1998 | Panayotatos ......... C07K 14/525 435/91.42 |
| 5,719,055 A | 2/1998 | Cooper |
| 5,770,359 A | 6/1998 | Wilson et al. |
| 5,827,739 A | 10/1998 | Wilson et al. |
| 5,843,742 A | 12/1998 | Natsoulis et al. |
| 5,914,267 A | 6/1999 | Mertz et al. |
| 5,958,775 A | 9/1999 | Wickstrom et al. |
| 5,965,443 A | 10/1999 | Reznikoff et al. |
| 5,968,785 A | 10/1999 | Devine et al. |
| 5,994,136 A | 11/1999 | Naldini et al. |
| 6,013,516 A | 1/2000 | Verma et al. |
| 6,027,722 A | 2/2000 | Hodgson |
| 6,136,597 A | 10/2000 | Hope et al. |
| 6,455,275 B1 | 9/2002 | Axel et al. |
| 6,852,510 B2 | 2/2005 | Bremel et al. |
| 7,332,333 B2 | 2/2008 | Bremel et al. |
| 9,567,578 B1 * | 2/2017 | Lee ...................... C12N 5/0686 |
| 2003/0224415 A1 * | 12/2003 | Bremel .................. C12N 15/86 435/456 |
| 2004/0235173 A1 | 11/2004 | Bleck et al. |
| 2007/0258962 A1 * | 11/2007 | Chatellard ............. C12N 15/85 435/320.1 |
| 2012/0258494 A1 | 10/2012 | Stitz |

(Continued)

FOREIGN PATENT DOCUMENTS

| | | |
|---|---|---|
| WO | WO 87/00195 | 1/1987 |
| WO | WO 90/03430 | 4/1990 |
| WO | WO 92/01070 | 1/1992 |

(Continued)

OTHER PUBLICATIONS

Logan, et al., "Integrated Self-Inactivating Lentiviral Vectors Produce Full-Length Genomic Transcripts Competent for Encapsidation and Integration" Journal of Virology. (2004) P8421-8436 (Year: 2004).*
International Search Report and Written Opinion for PCT/US19/64423. Mailed Apr. 22, 2020. 13 pages.
Agarwal et al., Oligodeoxynucleoside phosphoramidates and phosphorothioates as inhibitors of human immunodeficiency virus. Proc Natl Acad Sci U S A. Oct. 1988;85(19):7079-83.
Animal Cell Culture: A Practical Approach 2nd Ed., Rickwood, D. and Hames, B. D., eds. Oxford University Press, New York. 1992. TOC only. 8 pages.

(Continued)

*Primary Examiner* — Evelyn Y Pyla
*Assistant Examiner* — Katherine R Small
(74) *Attorney, Agent, or Firm* — Casimir Jones, S.C.; J. Mitchell Jones

(57) ABSTRACT

The present invention relates to vectors and their use to develop host cell lines for production of a protein of interest, and in particular to vectors which utilize a weak promoter to drive a selectable marker.

18 Claims, 15 Drawing Sheets
Specification includes a Sequence Listing.

(56) References Cited

U.S. PATENT DOCUMENTS

2016/0194660 A1\* 7/2016 Ye .................... C12N 15/85
435/69.6

FOREIGN PATENT DOCUMENTS

| WO | WO 93/03769 | 3/1993 |
| --- | --- | --- |
| WO | WO 99/14310 | 3/1999 |
| WO | WO 2004/070002 | 8/2004 |
| WO | WO 2005/024015 | 3/2005 |
| WO | WO 2017/118726 | 7/2017 |

OTHER PUBLICATIONS

Bleck. GPEx® A Flexible Method for the Rapid Generation of Stable, High Expressing, Antibody Producing Mammalian Cell Lines. Current Trends in Monoclonal Antibody Development and Manufacturing. 2010. Chpt 4. 51-62.

Bleck. An alternative method for the rapid generation of stable, high-expressing mammalian cell lines (A Technical Review). Bioprocessing J. Sep./Oct. 2006. pp 1-7.

Boshart et al., A very strong enhancer is located upstream of an immediate early gene of human cytomegalovirus. Cell. Jun. 1985;41(2):521-30.

Brun et al., The relationship of Piry virus to other vesiculoviruses: a re-evaluation based on the glycoprotein gene sequence. Intervirology. 1995;38(5):274-82.

Burns et al., Vesicular stomatitis virus G glycoprotein pseudotyped retroviral vectors: concentration to very high titer and efficient gene transfer into mammalian and nonmammalian cells. Proc Natl Acad Sci U S A. Sep. 1, 1993;90(17):8033-7.

Carter, Adeno-associated virus vectors. Curr Opin Biotechnol. Oct. 1992;3(5):533-9.

Cech et al., RNA catalysis by a group I ribozyme. Developing a model for transition state stabilization. J Biol Chem. Sep. 5, 1992;267(25):17479-82.

Cleveland et al., Routine large-scale production of monoclonal antibodies in a protein-free culture medium. J Immunol Methods. Jan. 28, 1983;56(2):221-34.

Craig, Transposon Tn7. Curr Top Microbiol Immunol. 1996;204:27-48.

De La Cruz et al., Characterization of the Tn5 transposase and inhibitor proteins: a model for the inhibition of transposition. J Bacteriol. Nov. 1993;175(21):6932-8.

Dijkema et al., Cloning and expression of the chromosomal immune interferon gene of the rat. Embo J. Mar. 1985;4(3):761-7.

Fan et al., Development of a highly-efficient CHO cell line generation system with engineered SV40E promoter. J Biotechnol. Dec. 2013;168(4):652-8.

Gorman et al., The Rous sarcoma virus long terminal repeat is a strong promoter when introduced into a variety of eukaryotic cells by DNA-mediated transfection. Proc Natl Acad Sci U S A. Nov. 1982;79(22):6777-81.

Graham et al., Characteristics of a human cell line transformed by DNA from human adenovirus type 5. J Gen Virol. Jul. 1977;36(1):59-74.

Han et al., Inhibition of Moloney murine leukemia virus-induced leukemia in transgenic mice expressing antisense RNA complementary to the retroviral packaging sequences. Proc Natl Acad Sci U S A. May 15, 1991;88(10):4313-7.

Heikkila et al., A c-myc antisense oligodeoxynucleotide inhibits entry into S phase but not progress from G0 to G1. Nature. Jul. 30-Aug. 5, 1987;328(6129):445-9.

Helene et al., Specific regulation of gene expression by antisense, sense and antigene nucleic acids. Biochim Biophys Acta. Jun. 21, 1990;1049(2):99-125.

Kim et al., Use of the human elongation factor 1α promoter as a versatile and efficient expression system. Gene, Jul. 16, 1990. vol. 91:217-223.

Kotin, Prospects for the use of adeno-associated virus as a vector for human gene therapy. Hum Gene Ther. Jul. 1994;5(7):793-801.

Lebkowski et al., Adeno-associated virus: a vector system for efficient introduction and integration of DNA into a variety of mammalian cell types. Mol Cell Biol. Oct. 1988;8(10):3988-96.

Logan et al., Integrated self-inactivating lentiviral vectors produce full-length genomic transcripts competent for encapsidation and integration. J Virol. Aug. 2004;78(16):8421-36.

Maniatis et al., Regulation of inducible and tissue-specific gene expression. Science. Jun. 5, 1987;236(4806):1237-45.

Markowitz et al., A safe packaging line for gene transfer: separating viral genes on two different plasmids. J Virol. Apr. 1988;62(4):1120-4.

Masters et al., Structure and expression of the glycoprotein gene of Chandipura virus. Virology. Jul. 1989;171(1):285-90.

Mastromarino et al., Characterization of membrane components of the erythrocyte involved in vesicular stomatitis virus attachment and fusion at acidic Ph. J Gen Virol. Sep. 1987;68 ( Pt 9):2359-69.

Mather et al., Culture of testicular cells in hormone-supplemented serum-free medium. Ann N Y Acad Sci. 1982;383:44-68.

Mather. Establishment and characterization of two distinct mouse testicular epithelial cell lines. Biol Reprod. Aug. 1980;23(1):243-52.

Mebatsion et al., Mokola virus glycoprotein and chimeric proteins can replace rabies virus glycoprotein in the rescue of infectious defective rabies virus particles. J Virol. Mar. 1995;69(3):1444-51.

Miller et al., Improved retroviral vectors for gene transfer and expression. Biotechniques. Oct. 1989;7(9):980-2, 984-6, 989-90.

Miller et al., Redesign of retrovirus packaging cell lines to avoid recombination leading to helper virus production. Mol Cell Biol. Aug. 1986;6(8):2895-902.

Mizushima et al., pEF-BOS, a powerful mammalian expression vector. Nucleic Acids Res. Sep. 11, 1990;18(17):5322.

Morisato et al., Tn10 transposition and circle formation in vitro. Cell. Oct. 9, 1987;51(1):101-11.

Muzyczka, Use of adeno-associated virus as a general transduction vector for mammalian cells. Curr Top Microbiol Immunol. 1992;158:97-129.

Naldini et al., In vivo gene delivery and stable transduction of nondividing cells by a lentiviral vector. Science. Apr. 12, 1996;272(5259):263-7.

NCBI HQ456316. Retroviral tet-shRNA expression vector TRMPV-ns, complete sequence Dec. 11, 2010 [online]. [Retrieved on Mar. 31, 2020] Retrieved from the Internet <URL:https://www.ncbi.nlm.nih.gov/nuccore/HQ456316.1/> nucleotides 4544-4969, 90.5% identity to Seq Id No. 3.

Pollok et al., Costimulation of transduced T lymphocytes via T cell receptor-CD3 complex and CD28 leads to increased transcription of integrated retrovirus. Hum Gene Ther. Sep. 1, 1999;10(13):2221-36.

Shelling et al., Targeted integration of transfected and infected adeno-associated virus vectors containing the neomycin resistance gene. Gene Ther. May 1994;1(3):165-9.

Uetsuki et al., Isolation and characterization of the human chromosomal gene for polypeptide chain elongation factor-1 alpha. J Biol Chem. Apr. 5, 1989;264(10):5791-8.

Uhlmann et al., Antisense oligonucleotides: a new therapeutic principle. Chem. Rev. 1990. 90:543-584.

Vincent et al., Vaccines 90. Cold Harbor Laboratory Press. 1990. 6 pages.

Voss et al., The role of enhancers in the regulation of cell-type-specific transcriptional control. Trends Biochem. Sci., Jul. 1986: 11:287.

Wilson et al., The structure of an antigenic determinant in a protein. Cell. Jul. 1984;37(3):767-78.

Zhou et al., Adeno-associated virus 2-mediated high efficiency gene transfer into immature and mature subsets of hematopoietic progenitor cells in human umbilical cord blood. J Exp Med. Jun. 1, 1994;179(6):1867-75.

\* cited by examiner

FIG. 3

```
LOCUS       CT041-LTR-LTR-se        6217 bp    DNA     linear       05-
FEATURES             Location/Qualifiers
     misc_feature    1..893
                     /note="hCMV-MoMuSV 5'LTR"
     misc_feature    963..1772
                     /note="Packaging Region"
     misc_feature    1789..2910
                     /note="GS cDNA"
     misc_feature    2912..3584
                     /note="sCMV Promoter"
     misc_feature    3667..4281
                     /note="Re-coded based on human KDR mRNA"
     misc_feature    3610..4965
                     /note="Anyway Coding DNA Sequence"
     misc_feature    4984..5584
                     /note="WPRE"
     misc_feature    5624..6217
                     /note="3' LTR"
     source          1..6217
                     /dnas_title="CT041-LTR-LTR-seq"

ORIGIN
        1 GTCCGGCCAT TAGCCATATT ATTCATTGGT TATATAGCAT AAATCAATAT TGGCTATTGG
       61 CCATTGCATA CGTTGTATCC ATATCATAAT ATGTACATTT ATATTGGCTC ATGTCCAACA
      121 TTACGCCCAT GTTGACATTG ATTATTGACT AGTTATTAAT AGTAATCAAT TACGGGGTCA
      181 TTAGTTCATA GCCCATATAT GGAGTTCCGC GTTACATAAC TTACGGTAAA TGGCCCGCCT
      241 GGCTGACCGC CCAACGACCC CCGCCCATTG ACGTCAATAA TGACGTATGT TCCCATAGTA
      301 ACGCCAATAG GGACTTTCCA TTGACGTCAA TGGGTGGAGT ATTTACGGTA AACTGCCCAC
      361 TTGGCAGTAC ATCAAGTGTA TCATATGCCA AGTACGCCCC CTATTGACGT CAATGACGGT
      421 AAATGGCCCG CCTGGCATTA TGCCCAGTAC ATGACCTTAT GGGACTTTCC TACTTGGCAG
      481 TACATCTACG TATTAGTCAT CGCTATTACC ATGGTGATGC GGTTTTGGCA GTACATCAAT
      541 GGGCGTGGAT AGCGGTTTGA CTCACGGGGA TTTCCAAGTC TCCACCCCAT TGACGTCAAT
      601 GGGAGTTTGT TTTGGCACCA AAATCAACGG GACTTTCCAA AATGTCGTAA CAACTCCGCC
      661 CCATTGACGC AAATGGGCGG TAGGCGTGTA CGGTGGGAGG TCTATATAAG CAGAGCTCAA
      721 TAAAAGAGCC CACAACCCCT CACTCGGCGC GCCAGTCTTC CGATAGACTG CGTCGCCCGG
      781 GTACCCGTAT TCCCAATAAA GCCTCTTGCT GTTTGCATCC GAATCGTGGT CTCGCTGTTC
      841 CTTGGGAGGG TCTCCTCTGA GTGATTGACT ACCCACGACG GGGGTCTTTC ATTTGGGGGC
      901 TCGTCCGGGA TTTGGAGACC CCTGCCCAGG GACCACCGAC CCACCACCGG GAGGTAAGCT
      961 GGCCAGCAAC TTATCTGTGT CTGTCCGATT GTCTAGTGTC TATGTTTGAT GTTATGCGCC
     1021 TGCGTCTGTA CTAGTTAGCT AACTAGCTCT GTATCTGGCG GACCCGTGGT GGAACTGACG
     1081 AGTTCTGAAC ACCCGGCCGC AACCCTGGGA GACGTCCCAG GGACTTTGGG GGCCGTTTTT
     1141 GTGGCCCGAC CTGAGGAAGG GAGTCGATGT GGAATCCGAC CCCGTCAGGA TATGTGGTTC
     1201 TGGTAGGAGA CGAGAACCTA AAACAGTTCC CGCCTCCGTC TGAATTTTTG CTTTCGGTTT
     1261 GGAACCGAAG CCGCGCGTCT TGTCTGCTGC AGCGCTGCAG CATCGTTCTG TGTTGTCTCT
     1321 GTCTGACTGT GTTTCTGTAT TTGTCTGAAA ATTAGGGCCA GACTGTTACC ACTCCCTTAA
     1381 GTTTGACCTT AGGTCACTGG AAAGATGTCG AGCGGATCGC TCACAACCAG TCGGTAGATG
     1441 TCAAGAAGAG ACGTTGGGTT ACCTTCTGCT CTGCAGAATG CCAACCTTT AACGTCGGAT
     1501 GGCCGCGAGA CGGCACCTTT AACCGAGACC TCATCACCCA GGTTAAGATC AAGGTCTTTT
     1561 CACCTGGCCC GCATGGACAC CCAGACCAGG TCCCCTACAT CGTGACCTGG GAAGCTTGG
     1621 CTTTTGACCC CCCTCCCTGG GTCAAGCCCT TTGTACACCC TAAGCCTCCG CCTCCTCTTC
     1681 CTCCATCCGC CCCGTCTCTC CCCCTTGAAC CTCCTCGTTC GACCCCGCCT CGATCCTCCC
     1741 TTTATCCAGC CCTCACTCCT TCTCTAGGCG CCGGAATTGC CTTCCACCAT GGCCACCTCA
     1801 GCAAGTTCCC ACTTGAACAA AAACATCAAG CAAATGTACT TGTGCCTGCC CAGGGTGAG
     1861 AAAGTCCAAG CCATGTATAT CTGGGTTGAT GGTACTGGAG AAGGACTGCG CTGCAAAACC
     1921 CGCACCCTGG ACTGTGAGCC CAAGTGTGTA GAAGAGTTAC CTGAGTGGAA TTTTGATGGC
     1981 TCTAGTACCT TCAGTCTGA GGGCTCCAAC AGTGACATGT ATCTCAGCCC TGTTGCCATG
```

FIG. 3 (cont'd)

```
2041 TTTCGGGACC CCTTCCGCAG AGATCCCAAC AAGCTGGTGT TCTGTGAAGT TTTCAAGTAC
2101 AACCGGAAGC CTGCAGAGAC CAATTTAAGG CACTCGTGTA AACGGATAAT GGACATGGTG
2161 AGCAACCAGC ACCCCTGGTT TGGAATGGAA CAGGAGTATA CTCTGATGGG AACAGATGGG
2221 CACCCTTTTG GTTGGCCTTC CAATGGCTTT CCTGGGCCCC AAGGTCCGTA TTACTGTGGT
2281 GTGGGCGCAG ACAAAGCCTA TGGCAGGGAT ATCGTGGAGG CTCACTACCG CGCCTGCTTG
2341 TATGCTGGGG TCAAGATTAC AGGAACAAAT GCTGAGGTCA TGCCTGCCCA GTGGGAGTTC
2401 CAAATAGGAC CCTGTGAAGG AATCCGCATG GGAGATCATC TCTGGGTGGC CCGTTTCATC
2461 TTGCATCGAG TATGTGAAGA CTTTGGGGTA ATAGCAACCT TGACCCCAA GCCCATTCCT
2521 GGGAACTGGA ATGGTGCAGG CTGCCATACC AACTTTAGCA CCAAGGCCAT GCGGGAGGAG
2581 AATGGTCTGA AGCACATCGA GGAGGCCATC GAGAAACTAA GCAAGCGGCA CCGGTACCAC
2641 ATTCGAGCCT ACGATCCCAA GGGGGGCCTG ACAATGCCC GTCGTCTGAC TGGGTTCCAC
2701 GAAACGTCCA ACATCAACGA CTTTTCTGCT GGTGTCGCCA ATCGCAGTGC CAGCATCCGC
2761 ATTCCCCGGA CTGTCGGCCA GGAGAAGAAA GGTTACTTTG AAGACCGCCG CCCCTCTGCC
2821 AACTGTGACC CCTTTGCAGT GACAGAAGCC ATCGTCCGCA CATGCCTTCT CAATGAGACT
2881 GGCGACGAGC CCTTCCAATA CAAAACTAA AGATCCCTAT GGCTATTGGC CAGGTTCAAT
2941 ACTATGTATT GGCCCTATGC CATATAGTAT TCCATATATG GGTTTTCCTA TTGACGTAGA
3001 TAGCCCCTCC CAATGGGCGG TCCCATATAC CATATATGGG GCTTCCTAAT ACCGCCCATA
3061 GCCACTCCCC CATTGACGTC AATGGTCTCT ATATATGGTC TTTCCTATTG ACGTCATATG
3121 GGCGGTCCTA TTGACGTATA TGGCGCCTCC CCCATTGACG TCAATTACGG TAAATGGCCC
3181 GCCTGGCTCA ATGCCCATTG ACGTCAATAG GACCACCCAC CATTGACGTC AATGGGATGG
3241 CTCATTGCCC ATTCATATCC GTTCTCACGC CCCCTATTGA CGTCAATGAC GGTAAATGGC
3301 CCACTTGGCA GTACATCAAT ATCTATTAAT AGTAACTTGG CAAGTACATT ACTATTGGAA
3361 GTACGCCAGG GTACATTGGC AGTACTCCCA TTGACGTCAA TGGCGGTAAA TGGCCCGCGA
3421 TGGCTGCCAA GTACATCCCC ATTGACGTCA ATGGGGAGGG GCAATGACGC AAATGGGCGT
3481 TCCATTGACG TAAATGGGCG GTAGGCGTGC CTAATGGGAG GTCTATATAA GCAATGCTCG
3541 TTTAGGGAAC CGCCATTCTG CCTGGGACG TCGGAGGAGC TCGAAAGCTT CTAGACAATT
3601 GCCGCCACCA TGATGTCCTT TGTCTCTCTG CTCCTGGTTG GCATCCTATT CCATGCCACC
3661 CAGGCCAGTG ATACAGGTAG ACCTTTCGTA GAGATGTACA GTGAAATCCC CGAAATTATA
3721 CACATGACTG AAGGAAGGGA GCTCGTCATT CCCTGCCGGG TTACGTCACC TAACATCACT
3781 GTTACTTTAA AAAAGTTTCC ACTTGACACT TGATCCCTG ATGGAAAACG CATAATCTGG
3841 GACAGTAGAA AGGGCTTCAT CATATCAAAT GCAACGTACA AAGAAATAGG CTTCTGACC
3901 TGTGAAGCAA CAGTCAATGG GCATTTGTAT AAGACAAACT ATCTCACACA TCGACAAACC
3961 AATACAATCA TAGATGTCGT TCTGAGTCCG TCTCATGAA TTGAACTATC TGTTGGAGAA
4021 AAGCTTGTCT TAAATTGTAC AGCAAGAACT GAACTAAATG TGGGGATTGA CTTCAACTGG
4081 GAATACCCTT CTTCGAAGCA TCAGCATAAG AAACTTGTAA ACCGAGACCT AAAAACCCAG
4141 TCTGGGAGTG AGATGAAGAA GTTTTTGAGC ACCTTAACTA TAGATGGTGT AACCCGGAGT
4201 GACCAAGGAT TGTACACCTG TGCAGCATCC AGTGGGCTGA TGACCAAGAA AACAGCACA
4261 TTTGTCAGGG TCCATGAAAA AGACAAAACT CACACATGCC CACCGTGCCC AGCACCTGAA
4321 CTCCTGGGGG GACCCTCAGT CTTCCTCTTC CCCCCAAAAC CCAAGGACAC CCTCATGATC
4381 TCCCGGACCC CTGAGGTCAC ATGCGTGGTG GTGGACGTGA GCCACGAAGA CCCTGAGGTC
4441 AAGTTCAACT GGTACGTGGA CGGCGTGGAG GTGCATAATG CCAAGACAAA GCCACGGGAG
4501 GAGCAGTACA ACAGCACATA TCGTGTGGTC AGCGTCCTCA CCGTCCTGCA CCAGGACTGG
4561 CTGAATGGCA AGGAGTACAA GTGCAAGGTC TCCAACAAAG CCCTCCCAGC CCCCATCGAG
4621 AAAACCATCT CCAAAGCCAA AGGGCAGCCC CGAGAACCAC AGGTGTACAC CCTGCCCCCA
4681 TCCCGGGATG AGCTGACCAA GAACCAGGTC AGCCTGACCT GCCTGGTCAA AGGCTTCTAT
4741 CCCAGCGACA TCGCCGTGGA GTGGGAGAGC AATGGGCAGC CGGAGAACAA CTACAAGACC
4801 ACGCCTCCCG TGCTGGACTC CGACGGCTCC TTCTTCCTCT ACAGCAAGCT CACCGTGGAC
4861 AAGAGCAGGT GGCAGCAGGG GAACGTCTTC TCATGCTCCG TGATGCATGA GGCTCTGCAC
4921 AACCACTACA CGCAGAAGAG CCTCTCCCTG TCTCCGGGA AATGATGAGA TCTCGAGTTC
4981 GACATCGATA ATCAACCTCT GGATTACAAA ATTTGTGAAA GATTGACTGG TATTCTTAAC
5041 TATGTTGCTC CTTTTACGCT ATGTGGATAC GCTGCTTTAA TGCCTTTGTA TCATGCTATT
5101 GCTTCCCGTA TGGCTTTCAT TTTCTCCTCC TTGTATAAAT CCTGGTTGCT GTCTCTTTAT
5161 GAGGAGTTGT GGCCCGTTGT CAGGCAACGT GGCGTGGTGT GCACTGTGTT GCTGACGCA
5221 ACCCCCACTG GTTGGGGCAT TGCCACCACC TGTCAGCTCC TTTCCGGGAC TTTCGCTTTC
5281 CCCCTCCCTA TTGCCACGGC GGAACTCATC GCCGCCTGCC TTGCCCGCTG CTGGACAGGG
5341 GCTCGGCTGT TGGGCACTGA CAATTCCGTG GTGTTGTCGG GGAAATCATC GTCCTTTCCT
5401 TGGCTGCTCG CCTGTGTTGC CACCTGGATT CTGCGCGGGA CGTCCTTCTG CTACGTCCCT
5461 TCGGCCCTCA ATCCAGCGGA CCTTCCTTCC CGCGGCCTGC TGCCGGCTCT GCGGCCTCTT
```

FIG. 3 (cont'd)

```
5521 CCGCGTCTTC GCCTTCGCCC TCAGACGAGT CGGATCTCCC TTTGGGCCGC CTCCCCGCAT
5581 CGATAAAATA AAAGATTTTA TTTAGTCTCC AGAAAAAGGG GGGAATGAAA GACCCCACCT
5641 GTAGGTTTGG CAAGCTAGCT TAAGTAACGC CATTTTGCAA GGCATGGAAA AATACATAAC
5701 TGAGAATAGA GAAGTTCAGA TCAAGGTCAG GAACAGATGG AACAGCTGAA TATGGGCCAA
5761 ACAGGATATC TGTGGTAAGC AGTTCCTGCC CCGGCTCAGG GCCAAGAACA GATGGAACAG
5821 CTGAATATGG GCCAAACAGG ATATCTGTGG TAAGCAGTTC CTGCCCCGGC TCAGGGCCAA
5881 GAACAGATGG TCCCCAGATG CGGTCCAGCC CTCAGCAGTT TCTAGAGAAC CATCAGATGT
5941 TTCCAGGGTG CCCCAAGGAC CTGAAATGAC CCTGTGCCTT ATTTGAACTA ACCAATCAGT
6001 TCGCTTCTCG CTTCTGTTCG CGCGCTTCTG CTCCCCGAGC TCAATAAAAG AGCCCACAAC
6061 CCCTCACTCG GGGCGCCAGT CCTCCGATTG ACTGAGTCGC CCGGGTACCC GTGTATCCAA
6121 TAAACCCTCT TGCAGTTGCA TCCGACTTGT GGTCTCGCTG TTCCTTGGGA GGGTCTCCTC
6181 TGAGTGATTG ACTACCCGTC AGCGGGGGTC TTTCATT
```

FIG. 4

```
LOCUS       CT051-LTR-LTR-se       6065 bp    DNA     linear      05-

FEATURES             Location/Qualifiers
    misc_feature     1..893
                     /note="hCMV-MoMuSV 5'LTR"
    misc_feature     963..1772
                     /note="Packaging Region"
    misc_feature     1789..2910
                     /note="GS cDNA"
    misc_feature     2912..3584
                     /note="sCMV Promoter"
    misc_feature     3667..4281
                     /note="Re-coded based on human KDR mRNA"
    misc_feature     3610..4965
                     /note="Anyway Coding DNA Sequence"
    misc_feature     4984..5584
                     /note="WPRE"
    misc_feature     5624..6065
                     /note="SIN 3' LTR"
    source           1..6065
                     /dnas_title="CT051-LTR-LTR-seq"

ORIGIN
        1 GTCCGGCCAT TAGCCATATT ATTCATTGGT TATATAGCAT AAATCAATAT TGGCTATTGG
       61 CCATTGCATA CGTTGTATCC ATATCATAAT ATGTACATTT ATATTGGCTC ATGTCCAACA
      121 TTACGCCCAT GTTGACATTG ATTATTGACT AGTTATTAAT AGTAATCAAT TACGGGGTCA
      181 TTAGTTCATA GCCCATATAT GGAGTTCCGC GTTACATAAC TTACGGTAAA TGGCCCGCCT
      241 GGCTGACCGC CCAACGACCC CCGCCCATTG ACGTCAATAA TGACGTATGT TCCCATAGTA
      301 ACGCCAATAG GGACTTTCCA TTGACGTCAA TGGGTGGAGT ATTTACGGTA AACTGCCCAC
      361 TTGGCAGTAC ATCAAGTGTA TCATATGCCA AGTACGCCCC CTATTGACGT CAATGACGGT
      421 AAATGGCCCG CCTGGCATTA TGCCCAGTAC ATGACCTTAT GGGACTTTCC TACTTGGCAG
      481 TACATCTACG TATTAGTCAT CGCTATTACC ATGGTGATGC GGTTTTGGCA GTACATCAAT
      541 GGGCGTGGAT AGCGGTTTGA CTCACGGGGA TTTCCAAGTC TCCACCCCAT TGACGTCAAT
      601 GGGAGTTTGT TTTGGCACCA AAATCAACGG GACTTTCCAA AATGTCGTAA CAACTCCGCC
      661 CCATTGACGC AAATGGGCGG TAGGCGTGTA CGGTGGGAGG TCTATATAAG CAGAGCTCAA
      721 TAAAAGAGCC CACAACCCCT CACTCGGCGC GCCAGTCTTC CGATAGACTG CGTCGCCCGG
      781 GTACCCGTAT TCCCAATAAA GCCTCTTGCT GTTTGCATCC GAATCGTGGT CTCGCTGTTC
      841 CTTGGGAGGG TCTCCTCTGA GTGATTGACT ACCCACGACG GGGGTCTTTC ATTTGGGGGC
      901 TCGTCCGGGA TTTGGAGACC CCTGCCCAGG GACCACCGAC CCACCACCGG GAGGTAAGCT
      961 GGCCAGCAAC TTATCTGTGT CTGTCCGATT GTCTAGTGTC TATGTTTGAT GTTATGCGCC
     1021 TGCGTCTGTA CTAGTTAGCT AACTAGCTCT GTATCTGGCG GACCCGTGGT GGAACTGACG
     1081 AGTTCTGAAC ACCCGGCCGC AACCCTGGGA GACGTCCCAG GGACTTTGGG GGCCGTTTTT
     1141 GTGGCCCGAC CTGAGGAAGG GAGTCGATGT GGAATCCGAC CCCGTCAGGA TATGTGGTTC
     1201 TGGTAGGAGA CGAGAACCTA AAACAGTTCC CGCCTCCGTC TGAATTTTTG CTTTCGGTTT
     1261 GGAACCGAAG CCGCGCGTCT TGTCTGCTGC AGCGCTGCAG CATCGTTCTG TGTTGTCTCT
     1321 GTCTGACTGT GTTTCTGTAT TTGTCTGAAA ATTAGGGCCA GACTGTTACC ACTCCCTTAA
     1381 GTTTGACCTT AGGTCACTGG AAAGATGTCG AGCGGATCGC TCACAACCAG TCGGTAGATG
     1441 TCAAGAAGAG ACGTTGGGTT ACCTTCTGCT CTGCAGAATG CCAACCTTT AACGTCGGAT
     1501 GGCCGCGAGA CGGCACCTTT AACCGAGACC TCATCACCCA GGTTAAGATC AAGGTCTTTT
     1561 CACCTGGCCC GCATGGACAC CCAGACCAGG TCCCCTACAT CGTGACCTGG GAAGCTTGG
     1621 CTTTTGACCC CCCTCCCTGG GTCAAGCCCT TTGTACACCC TAAGCCTCCG CCTCCTCTTC
     1681 CTCCATCCGC CCCGTCTCTC CCCCTTGAAC CTCCTCGTTC GACCCCGCCT CGATCCTCCC
     1741 TTTATCCAGC CCTCACTCCT TCTCTAGGCG CCGGAATTGC CTTCCACCAT GGCCACCTCA
     1801 GCAAGTTCCC ACTTGAACAA AAACATCAAG CAAATGTACT TGTGCCTGCC CAGGGTGAG
     1861 AAAGTCCAAG CCATGTATAT CTGGGTTGAT GGTACTGGAG AAGGACTGCG CTGCAAAACC
     1921 CGCACCCTGG ACTGTGAGCC CAAGTGTGTA GAAGAGTTAC CTGAGTGGAA TTTTGATGGC
     1981 TCTAGTACCT TCAGTCTGA GGGCTCCAAC AGTGACATGT ATCTCAGCCC TGTTGCCATG
```

FIG. 4 (cont'd)

```
2041 TTTCGGGACC CCTTCCGCAG AGATCCCAAC AAGCTGGTGT TCTGTGAAGT TTTCAAGTAC
2101 AACCGGAAGC CTGCAGAGAC CAATTTAAGG CACTCGTGTA AACGGATAAT GGACATGGTG
2161 AGCAACCAGC ACCCCTGGTT TGGAATGGAA CAGGAGTATA CTCTGATGGG AACAGATGGG
2221 CACCCTTTTG GTTGGCCTTC CAATGGCTTT CCTGGGCCCC AAGGTCCGTA TTACTGTGGT
2281 GTGGGCGCAG ACAAAGCCTA TGGCAGGGAT ATCGTGGAGG CTCACTACCG CGCCTGCTTG
2341 TATGCTGGGG TCAAGATTAC AGGAACAAAT GCTGAGGTCA TGCCTGCCCA GTGGGAGTTC
2401 CAAATAGGAC CCTGTGAAGG AATCCGCATG GGAGATCATC TCTGGGTGGC CCGTTTCATC
2461 TTGCATCGAG TATGTGAAGA CTTTGGGGTA ATAGCAACCT TTGACCCCAA GCCCATTCCT
2521 GGGAACTGGA ATGGTGCAGG CTGCCATACC AACTTTAGCA CCAAGGCCAT GCGGGAGGAG
2581 AATGGTCTGA AGCACATCGA GGAGGCCATC GAGAAACTAA GCAAGCGGCA CCGGTACCAC
2641 ATTCGAGCCT ACGATCCCAA GGGGGGCCTG GACAATGCCC GTCGTCTGAC TGGGTTCCAC
2701 GAAACGTCCA ACATCAACGA CTTTTCTGCT GGTGTCGCCA ATCGCAGTGC CAGCATCCGC
2761 ATTCCCCGGA CTGTCGGCCA GGAGAAGAAA GGTTACTTTG AAGACCGCCG CCCCTCTGCC
2821 AACTGTGACC CCTTTGCAGT GACAGAAGCC ATCGTCCGCA CATGCCTTCT CAATGAGACT
2881 GGCGACGAGC CCTTCCAATA CAAAACTAAA AGATCCCTAT GGCTATTGGC CAGGTTCAAT
2941 ACTATGTATT GGCCCTATGC CATATAGTAT TCCATATATG GGTTTTCCTA TTGACGTAGA
3001 TAGCCCCTCC CAATGGGCGG TCCCATATAC CATATATGGG GCTTCCTAAT ACCGCCCATA
3061 GCCACTCCCC CATTGACGTC AATGGTCTCT ATATATGGTC TTTCCTATTG ACGTCATATG
3121 GGCGGTCCTA TTGACGTATA TGGCGCCTCC CCCATTGACG TCAATTACGG TAAATGGCCC
3181 GCCTGGCTCA ATGCCCATTG ACGTCAATAG GACCACCCAC CATTGACGTC AATGGGATGG
3241 CTCATTGCCC ATTCATATCC GTTCTCACGC CCCCTATTGA CGTCAATGAC GGTAAATGGC
3301 CCACTTGGCA GTACATCAAT ATCTATTAAT AGTAACTTGG CAAGTACATT ACTATTGGAA
3361 GTACGCCAGG GTACATTGGC AGTACTCCCA TTGACGTCAA TGGCGGTAAA TGGCCCGCGA
3421 TGGCTGCCAA GTACATCCCC ATTGACGTCA ATGGGGAGGG GCAATGACGC AAATGGGCGT
3481 TCCATTGACG TAAATGGGCG GTAGGCGTGC CTAATGGGAG GTCTATATAA GCAATGCTCG
3541 TTTAGGGAAC CGCCATTCTG CCTGGGGACG TCGGAGGAGC TCGAAAGCTT CTAGACAATT
3601 GCCGCCACCA TGATGTCCTT TGTCTCTCTG CTCCTGGTTG GCATCCTATT CCATGCCACC
3661 CAGGCCAGTG ATACAGGTAG ACCTTTCGTA GAGATGTACA GTGAAATCCC CGAAATTATA
3721 CACATGACTG AAGGAAGGGA GCTCGTCATT CCCTGCCGGG TTACGTCACC TAACATCACT
3781 GTTACTTTAA AAAAGTTTCC ACTTGACACT TTGATCCCTG ATGGAAAACG CATAATCTGG
3841 GACAGTAGAA AGGGCTTCAT CATATCAAAT GCAACGTACA AAGAAATAGG GCTTCTGACC
3901 TGTGAAGCAA CAGTCAATGG GCATTTGTAT AAGACAAACT ATCTCACACA TCGACAAACC
3961 AATACAATCA TAGATGTCGT TCTGAGTCCG TCTCATGGAA TTGAACTATC TGTTGGAGAA
4021 AAGCTTGTCT TAAATTGTAC AGCAAGAACT GAACTAAATG TGGGGATTGA CTTCAACTGG
4081 GAATACCCTT CTTCGAAGCA TCAGCATAAG AAACTTGTAA ACCGAGACCT AAAAACCCAG
4141 TCTGGGAGTG AGATGAAGAA GTTTTTGAGC ACCTTAACTA TAGATGGTGT AACCCGGAGT
4201 GACCAAGGAT TGTACACCTG TGCAGCATCC AGTGGGCTGA TGACCAAGAA AAACAGCACA
4261 TTTGTCAGGG TCCATGAAAA AGACAAAACT CACACATGCC CACCGTGCCC AGCACCTGAA
4321 CTCCTGGGGG GACCCTCAGT CTTCCTCTTC CCCCCAAAAC CCAAGGACAC CCTCATGATC
4381 TCCCGGACCC CTGAGGTCAC ATGCGTGGTG GTGGACGTGA GCCACGAAGA CCCTGAGGTC
4441 AAGTTCAACT GGTACGTGGA CGGCGTGGAG GTGCATAATG CCAAGACAAA GCCACGGGAG
4501 GAGCAGTACA ACAGCACATA TCGTGTGGTC AGCGTCCTCA CCGTCCTGCA CCAGGACTGG
4561 CTGAATGGCA AGGAGTACAA GTGCAAGGTC TCCAACAAAG CCCTCCCAGC CCCCATCGAG
4621 AAAACCATCT CCAAAGCCAA AGGGCAGCCC CGAGAACCAC AGGTGTACAC CCTGCCCCCA
4681 TCCCGGGATG AGCTGACCAA GAACCAGGTC AGCCTGACCT GCCTGGTCAA AGGCTTCTAT
4741 CCCAGCGACA TCGCCGTGGA GTGGGAGAGC AATGGGCAGC CGGAGAACAA CTACAAGACC
4801 ACGCCTCCCG TGCTGGACTC CGACGGCTCC TTCTTCCTCT ACAGCAAGCT CACCGTGGAC
4861 AAGAGCAGGT GGCAGCAGGG GAACGTCTTC TCATGCTCCG TGATGCATGA GGCTCTGCAC
4921 AACCACTACA CGCAGAAGAG CCTCTCCCTG TCTCCCGGGA AATGATGAGA CTCGAGTTC
4981 GACATCGATA ATCAACCTCT GGATTACAAA ATTTGTGAAA GATTGACTGG TATTCTTAAC
5041 TATGTTGCTC CTTTTACGCT ATGTGGATAC GCTGCTTTAA TGCCTTTGTA TCATGCTATT
5101 GCTTCCCGTA TGGCTTTCAT TTTCTCCTCC TTGTATAAAT CCTGGTTGCT GTCTCTTTAT
5161 GAGGAGTTGT GGCCCGTTGT CAGGCAACGT GGCGTGGTGT GCACTGTGTT TGCTGACGCA
5221 ACCCCCACTG GTTGGGGCAT TGCCACCACC TGTCAGCTCC TTTCCGGGAC TTTCGCTTTC
5281 CCCCTCCCTA TTGCCACGGC GGAACTCATC GCCGCCTGCC TTGCCCGCTG CTGGACAGGG
5341 GCTCGGCTGT TGGGCACTGA CAATTCCGTG GTGTTGTCGG GGAAATCATC GTCCTTTCCT
5401 TGGCTGCTCG CCTGTGTTGC CACCTGGATT CTGCGCGGGA CGTCCTTCTG CTACGTCCCT
5461 TCGGCCCTCA ATCCAGCGGA CCTTCCTTCC CGCGGCCTGC TGCCGGCTCT GCGGCCTCTT
```

FIG. 4 (cont'd)

```
5521 CCGCGTCTTC GCCTTCGCCC TCAGACGAGT CGGATCTCCC TTTGGGCCGC CTCCCCGCAT
5581 CGATAAAATA AAAGATTTTA TTTAGTCTCC AGAAAAAGGG GGGAATGAAA GACCCCACCT
5641 GTAGGTTTGG CAAGCTAGCT TAAGTAACGC CATTTTGCAA GGCATGGAAA AATACATAAC
5701 TGAGAATAGA GAAGTTCAGA TCAAGGTCAG GAACAGATGG AACAGGGTCG ACCGGTCGAC
5761 CGGTCGACCC TAGAGAACCA TCAGATGTTT CCAGGGTGCC CCAAGGACCT GAAATGACCC
5821 TGTGCCTTAT TTGAACTAAC CAATCAGTTC GCTTCTCGCT TCTGTTCGCG CGCTTCTGCT
5881 CCCCGAGCTC AATAAAAGAG CCCACAACCC CTCACTCGGG GCGCCAGTCC TCCGATTGAC
5941 TGAGTCGCCC GGGTACCCGT GTATCCAATA AACCCTCTTG CAGTTGCATC CGACTTGTGG
6001 TCTCGCTGTT CCTTGGGAGG GTCTCCTCTG AGTGATTGAC TACCCGTCAG CGGGGGTCTT
6061 TCATT
```

FIG. 7

```
AATGAAA GACCCCACCT GTAGGTTTGG CAAGCTAGCT TAAGTAACGC CATTTTGCAA GGCATGGAAA
AATACATAAC TGAGAATAGA GAAGTTCAGA TCAAGGTCAG GAACAGATGG AACAGGGTCG
ACCGGTCGAC CGGTCGACCC TAGAGAACCA TCAGATGTTT CCAGGGTGCC CCAAGGACCT
GAAATGACCC TGTGCCTTAT TTGAACTAAC CAATCAGTTC GCTTCTCGCT TCTGTTCGCG
CGCTTCTGCT CCCCGAGCTC AATAAAAGAG CCCACAACCC CTCACTCGGG GCGCCAGTCC
TCCGATTGAC TGAGTCGCCC GGGTACCCGT GTATCCAATA AACCCTCTTG CAGTTGCATC
CGACTTGTGG TCTCGCTGTT CCTTGGGAGG GTCTCCTCTG AGTGATTGAC TACCCGTCAG
CGGGGGTCTT TCATT
```

FIG. 9 (SEQ ID NO:4)

```
1    TCGCGCGTTT CGGTGATGAC GGTGAAAACC TCTGACACAT GCAGCTCCCG GAGACGGTCA
61   CAGCTTGTCT GTAAGCGGAT GCCGGGAGCA GACAAGCCCG TCAGGGCGCG TCAGCGGGTG
121  TTGGCGGGTG TCGGGGCTGG CTTAACTATG CGGCATCAGA GCAGATTGTA CTGAGAGTGC
181  ACCATATGCG GTGTGAAATA CCGCACAGAT GCGTAAGGAG AAAATACCGC ATCAGGCGCC
241  ATTCGCCATT CAGGCTGCGC AACTGTTGGG AAGGGCGATC GGTGCGGGCC TCTTCGCTAT
301  TACGCCAGCT GGCGAAAGGG GGATGTGCTG CAAGGCGATT AAGTTGGGTA ACGCCAGGGT
361  TTTCCCAGTC ACGACGTTGT AAAACGACGG CCAGTGAATT CATTTAAATG AAAGACCCCA
421  CCTGTAGGTT TGGCAAGCTA GCTTAAGTAA CGCCATTTTG CAAGGCATGG AAAAATACAT
481  AACTGAGAAT AGAAAAGTTC AGATCAAGGT CAGGAACAGA TGGAACAGGG TCGACCGGTC
541  GACCGGTCGA CCCTAGAGAA CCATCAGATG TTTCCAGGGT GCCCCAAGGA CCTGAAATGA
601  CCCTGTGCCT TATTTGAACT AACCAATCAG TTCGCTTCTC GCTTCTGTTC GCGCGCTTCT
661  GCTCCCCGAG CTCAATAAAA GAGCCCACAA CCCCTCACTC GGGGCGCCAG TCTTCCGATA
721  GACTGCGTCG CCCGGGTACC CGTATTCCCA ATAAAGCCTC TTGCTGTTTG CATCCGAATC
781  GTGGTCTCGC TGTTCCTTGG GAGGGTCTCC TCTGAGTGAT TGACTACCCA CGACGGGGGT
841  CTTTCATTTG GGGGCTCGTC CGGGATTTGG AGACCCCTGC CCAGGGACCA CCGACCCACC
901  ACCGGGAGGT AAGCTGGCCA GCAACTTATC TGTGTCTGTC CGATTGTCTA GTGTCTATGT
961  TTGATGTTAT GCGCCTGCGT CTGTACTAGT TAGCTAACTA GCTCTGTATC TGGCGGACCC
1021 GTGGTGGAAC TGACGAGTTC TGAACACCCG GCCGCAACCC TGGGAGACGT CCCAGGGACT
1081 TTGGGGGCCG TTTTTGTGGC CCGACCTGAG GAAGGGAGTC GATGTGGAAT CCGACCCCGT
1141 CAGGATATGT GGTTCTGGTA GGAGACGAGA ACCTAAAACA GTTCCCGCCT CCGTCTGAAT
1201 TTTTGCTTTC GGTTTGGAAC CGAAGCCGCG CGTCTTGTCT GCTGCAGCGC TGCAGCATCG
1261 TTCTGTGTTG TCTCTGTCTG ACTGTGTTTC TGTATTTGTC TGAAAATTAG GGCCAGACTG
1321 TTACCACTCC CTTAAGTTTG ACCTTAGGTC ACTGGAAAGA TGTCGAGCGG ATCGCTCACA
1381 ACCAGTCGGT AGATGTCAAG AAGAGACGTT GGGTTACCTT CTGCTCTGCA GAATGGCCAA
1441 CCTTTAACGT CGGATGGCCG CGAGACGGCA CCTTTAACCG AGACCTCATC ACCCAGGTTA
1501 AGATCAAGGT CTTTTCACCT GGCCCGCATG GACACCCAGA CCAGGTCCCC TACATCGTGA
1561 CCTGGGAAGC CTTGGCTTTT GACCCCCCTC CCTGGGTCAA GCCCTTTGTA CACCCTAAGC
1621 CTCCGCCTCC TCTTCCTCCA TCCGCCCCGT CTCTCCCCCT TGAACCTCCT CGTTCGACCC
1681 CGCCTCGATC CTCCCTTTAT CCAGCCCTCA CTCCTTCTCT AGGCGCCGGA ATTGCTTCC
1741 ACCATGGCCA CCTCAGCAAG TTCCCACTTG AACAAAAACA TCAAGCAAAT GTACTTGTGC
1801 CTGCCCCAGG GTGAGAAAGT CCAAGCCATG TATATCTGGG TTGATGGTAC TGGAGAAGGA
1861 CTGCGCTGCA AAACCCGCAC CCTGGACTGT GAGCCCAAGT GTGTAGAAGA GTTACCTGAG
1921 TGGAATTTTG ATGGCTCTAG TACCTTTCAG TCTGAGGGCT CCAACAGTGA CATGTATCTC
1981 AGCCCTGTTG CCATGTTTCG GGACCCCTTC CGCAGAGATC CCAACAAGCT GGTGTTCTGT
2041 GAAGTTTTCA AGTACAACCG GAAGCCTGCA GAGACCAATT TAAGGCACTC GTGTAAACGG
2101 ATAATGGACA TGGTGAGCAA CCAGCACCCC TGGTTTGGAA TGGAACAGGA GTATACTCTG
2161 ATGGGAACAG ATGGGCACCC TTTTGGTTGG CCTTCCAATG GCTTTCCTGG GCCCCAAGGT
2221 CCGTATTACT GTGGTGTGGG CGCAGACAAA GCCTATGGCA GGGATATCGT GGAGGCTCAC
2281 TACCGCGCCT GCTTGTATGC TGGGGTCAAG ATTACAGGAA CAAATGCTGA GGTCATGCCT
2341 GCCCAGTGGG AGTTCCAAAT AGGACCCTGT GAAGGAATCC GCATGGGAGA TCATCTCTGG
2401 GTGGCCCGTT TCATCTTGCA TCGAGTATGT GAAGACTTTG GGGTAATAGC AACCTTTGAC
2461 CCCAAGCCCA TTCCTGGGAA CTGGAATGGT GCAGGCTGCC ATACCAACTT TAGCACCAAG
2521 GCCATGCGGG AGGAGAATGG TCTGAAGCAC ATCGAGGAGG CCATCGAGAA ACTAAGCAAG
2581 CGGCACCGGT ACCACATTCG AGCCTACGAT CCCAAGGGGG GCCTGGACAA TGCCCGTCGT
2641 CTGACTGGGT TCCACGAAAC GTCCAACATC AACGACTTTT CTGCTGGTGT CGCCAATCGC
2701 AGTGCCAGCA TCCGCATTCC CCGGACTGTC GGCCAGGAGA AGAAGGTTA CTTTGAAGAC
2761 CGCCGCCCCT CTGCCAACTG TGACCCCTTT GCAGTGACAG AAGCCATCGT CCGCACATGC
2821 CTTCTCAATG AGACTGGCGA CGAGCCCTTC CAATACAAAA ACTAAAGATC CCTATGGCTA
2881 TTGGCCAGGT TCAATACTAT GTATTGGCCC TATGCCATAT AGTATTCCAT ATATGGGTTT
2941 TCCTATTGAC GTAGATAGCC CCTCCCAATG GGCGGTCCCA TATACCATAT ATGGGGCTTC
3001 CTAATACCGC CCATAGCCAC TCCCCATTG ACGTCAATGG TCTCTATATA TGGTCTTTCC
3061 TATTGACGTC ATATGGGCGG TCCTATTGAC GTATATGGCG CCTCCCCCAT TGACGTCAAT
3121 TACGGTAAAT GGCCCGCCTG GCTCAATGCC CATTGACGTC AATAGGACCA CCCACCATTG
3181 ACGTCAATGG GATGGCTCAT TGCCCATTCA TATCCGTTCT CACGCCCCCT ATTGACGTCA
3241 ATGACGGTAA ATGGCCCACT TGGCAGTACA TCAATATCTA TTAATAGTAA CTTGGCAAGT
3301 ACATTACTAT TGGAAGTACG CCAGGGTACA TTGGCAGTAC TCCCATTGAC GTCAATGGCG
3361 GTAAATGGCC CGCGATGGCT GCCAAGTACA TCCCCATTGA CGTCAATGGG AGGGGCAAT
3421 GACGCAAATG GCGTTCCAT TGACGTAAAT GGCGGTAGG CGTGCCTAAT GGGAGGTCTA
3481 TATAAGCAAT GCTCGTTTAG GAACCGCCA TTCTGCCTGG GACGTCGGA GGAGCTCGAA
```

FIG. 9 (SEQ ID NO:4) cont'

```
3541 AGCTTCTAGA CAATTGCCGC CACCATGATG TCCTTTGTCT CTCTGCTCCT GGTTGGCATC
3601 CTATTCCATG CCACCCAGGC CAGTGATACA GGTAGACCTT TCGTAGAGAT GTACAGTGAA
3661 ATCCCCGAAA TTATACACAT GACTGAAGGA AGGGAGCTCG TCATTCCCTG CCGGGTTACG
3721 TCACCTAACA TCACTGTTAC TTTAAAAAAG TTTCCACTTG ACACTTTGAT CCCTGATGGA
3781 AAACGCATAA TCTGGGACAG TAGAAAGGGC TTCATCATAT CAAATGCAAC GTACAAAGAA
3841 ATAGGGCTTC TGACCTGTGA AGCAACAGTC AATGGGCATT TGTATAAGAC AAACTATCTC
3901 ACACATCGAC AAACCAATAC AATCATAGAT GTCGTTCTGA GTCCGTCTCA TGGAATTGAA
3961 CTATCTGTTG GAGAAAAGCT TGTCTTAAAT TGTACAGCAA GAACTGAACT AAATGTGGGG
4021 ATTGACTTCA ACTGGGAATA CCCTTCTTCG AAGCATCAGC ATAAGAAACT TGTAAACCGA
4081 GACCTAAAAA CCCAGTCTGG GAGTGAGATG AAGAAGTTTT TGAGCACCTT AACTATAGAT
4141 GGTGTAACCC GGAGTGACCA AGGATTGTAC ACCTGTGCAG CATCCAGTGG GCTGATGACC
4201 AAGAAAAACA GCACATTTGT CAGGGTCCAT GAAAAAGACA AAACTCACAC ATGCCCACCG
4261 TGCCCAGCAC CTGAACTCCT GGGGGGACCC TCAGTCTTCC TCTTCCCCCC AAAACCCAAG
4321 GACACCCTCA TGATCTCCCG GACCCCTGAG GTCACATGCG TGGTGGTGGA CGTGAGCCAC
4381 GAAGACCCTG AGGTCAAGTT CAACTGGTAC GTGGACGGCG TGGAGGTGCA TAATGCCAAG
4441 ACAAAGCCAC GGGAGGAGCA GTACAACAGC ACATATCGTG TGGTCAGCGT CCTCACCGTC
4501 CTGCACCAGG ACTGGCTGAA TGGCAAGGAG TACAAGTGCA AGGTCTCCAA CAAAGCCCTC
4561 CCAGCCCCCA TCGAGAAAAC CATCTCCAAA GCCAAAGGGC AGCCCCGAGA ACCACAGGTG
4621 TACACCCTGC CCCCATCCCG GGATGAGCTG ACCAAGAACC AGGTCAGCCT GACCTGCCTG
4681 GTCAAAGGCT TCTATCCCAG CGACATCGCC GTGGAGTGGG AGAGCAATGG GCAGCCGGAG
4741 AACAACTACA AGACCACGCC TCCCGTGCTG GACTCCGACG GCTCCTTCTT CCTCTACAGC
4801 AAGCTCACCG TGGACAAGAG CAGGTGGCAG CAGGGGAACG TCTTCTCATG CTCCGTGATG
4861 CATGAGGCTC TGCACAACCA CTACACGCAG AAGAGCCTCT CCCTGTCTCC GGGAAATGA
4921 TGAGATCTCG AGTTCGACAT CGATAATCAA CCTCTGGATT ACAAAATTTG TGAAAGATTG
4981 ACTGGTATTC TTAACTATGT TGCTCCTTTT ACGCTATGTG GATACGCTGC TTTAATGCCT
5041 TTGTATCATG CTATTGCTTC CCGTATGGCT TTCATTTTCT CCTCCTTGTA TAAATCCTGG
5101 TTGCTGTCTC TTTATGAGGA GTTGTGGCCC GTTGTCAGGC AACGTGGCGT GGTGTGCACT
5161 GTGTTTGCTG ACGCAACCCC CACTGGTTGG GGCATTGCCA CCACCTGTCA GCTCCTTTCC
5221 GGGACTTTCG CTTTCCCCCT CCCTATTGCC ACGGCGGAAC TCATCGCCGC CTGCCTTGCC
5281 CGCTGCTGGA CAGGGGCTCG GCTGTTGGGC ACTGACAATT CCGTGGTGTT GTCGGGGAAA
5341 TCATCGTCCT TTCCTTGGCT GCTCGCCTGT GTTGCCACCT GGATTCTGCG CGGGACGTCC
5401 TTCTGCTACG TCCCTTCGGC CCTCAATCCA GCGGACCTTC CTTCCCGCGG CCTGCTGCCG
5461 GCTCTGCGGC CTCTTCCGCG TCTTCGCCTT CGCCCTCAGA CGAGTCGGAT CTCCCTTTGG
5521 GCCGCCTCCC CGCATCGATG GGGGAGGCTA ACTGAAACAC GGAAGGAGAC AATACCGGAA
5581 GGAACCCGCG CTATGACGGC AATAAAAAGA CAGAATAAAA CGCACGGGTG TTGGGTCGTT
5641 TGTTCATAAA CGCGGGGTTC GGTCCCAGGG CTGGCACTCT GTCGATACCC CACCGAGACC
5701 CCATTGGGGC CAATACGCCC GCGTTTCTTC CTTTTCCCCA CCCCACCCCC CAAGTTCGGG
5761 TGAAGGCCCA GGGCTCGCAG CCAACGTCGG GGCGGCAGGC CCTGCCATAG CGGATCCTTT
5821 CCACTGTACG CGTAGCTTGG CGTAATCATG GTCATAGCTG TTTCCTGTGT GAAATTGTTA
5881 TCCGCTCACA ATTCCACACA ACATACGAGC CGGAAGCATA AAGTGTAAAG CCTGGGGTGC
5941 CTAATGAGTG AGCTAACTCA CATTAATTGC GTTGCGCTCA CTGCCCGCTT TCCAGTCGGG
6001 AAACCTGTCG TGCCAGCTGC ATTAATGAAT CGGCCAACGC GCGGGGAGAG GCGGTTTGCG
6061 TATTGGGCGC TCTTCCGCTT CCTCGCTCAC TGACTCGCTG CGCTCGGTCG TTCGGCTGCG
6121 GCGAGCGGTA TCAGCTCACT CAAAGGCGGT AATACGGTTA TCCACAGAAT CAGGGGATAA
6181 CGCAGGAAAG AACATGTGAG CAAAAGGCCA GCAAAAGGCC AGGAACCGTA AAAAGGCCGC
6241 GTTGCTGGCG TTTTTCCATA GGCTCCGCCC CCTGACGAG CATCACAAAA ATCGACGCTC
6301 AAGTCAGAGG TGGCGAAACC CGACAGGACT ATAAAGATAC CAGGCGTTTC CCCCTGGAAG
6361 CTCCCTCGTG CGCTCTCCTG TTCCGACCCT GCCGCTTACC GGATACCTGT CCGCCTTTCT
6421 CCCTTCGGGA AGCGTGGCGC TTTCTCATAG CTCACGCTGT AGGTATCTCA GTTCGGTGTA
6481 GGTCGTTCGC TCCAAGCTGG GCTGTGTGCA CGAACCCCCC GTTCAGCCCG ACCGCTGCGC
6541 CTTATCCGGT AACTATCGTC TTGAGTCCAA CCCGGTAAGA CACGACTTAT CGCCACTGGC
6601 AGCAGCCACT GGTAACAGGA TTAGCAGAGC GAGGTATGTA GGCGGTGCTA CAGAGTTCTT
6661 GAAGTGGTGG CCTAACTACG GCTACACTAG AAGAACAGTA TTTGGTATCT GCGCTCTGCT
6721 GAAGCCAGTT ACCTTCGGAA AAAGAGTTGG TAGCTCTTGA TCCGGCAAAC AAACCACCGC
6781 TGGTAGCGGT GGTTTTTTTG TTTGCAAGCA GCAGATTACG CGCAGAAAAA AAGGATCTCA
6841 AGAAGATCCT TTGATCTTTT CTACGGGGTC TGACGCTCAG TGGAACGAAA ACTCACGTTA
6901 AGGGATTTTG GTCATGAGAT TATCAAAAAG GATCTTCACC TAGATCCTTT TAAATTAAAA
6961 ATGAAGTTTT AAATCAATCT AAAGTATATA TGAGTAAACT TGGTCTGACA GTTACCAATG
```

FIG. 9 (SEQ ID NO:4) cont'

```
7021 CTTAATCAGT GAGGCACCTA TCTCAGCGAT CTGTCTATTT CGTTCATCCA TAGTTGCCTG
7081 ACTCCCCGTC GTGTAGATAA CTACGATACG GGAGGGCTTA CCATCTGGCC CCAGTGCTGC
7141 AATGATACCG CGAGACCCAC GCTCACCGGC TCCAGATTTA TCAGCAATAA ACCAGCCAGC
7201 CGGAAGGGCC GAGCGCAGAA GTGGTCCTGC AACTTTATCC GCCTCCATCC AGTCTATTAA
7261 TTGTTGCCGG GAAGCTAGAG TAAGTAGTTC GCCAGTTAAT AGTTTGCGCA ACGTTGTTGC
7321 CATTGCTACA GGCATCGTGG TGTCACGCTC GTCGTTTGGT ATGGCTTCAT TCAGCTCCGG
7381 TTCCCAACGA TCAAGGCGAG TTACATGATC CCCCATGTTG TGCAAAAAAG CGGTTAGCTC
7441 CTTCGGTCCT CCGATCGTTG TCAGAAGTAA GTTGGCCGCA GTGTTATCAC TCATGGTTAT
7501 GGCAGCACTG CATAATTCTC TTACTGTCAT GCCATCCGTA AGATGCTTTT CTGTGACTGG
7561 TGAGTACTCA ACCAAGTCAT TCTGAGAATA GTGTATGCGG CGACCGAGTT GCTCTTGCCC
7621 GGCGTCAATA CGGGATAATA CCGCGCCACA TAGCAGAACT TTAAAAGTGC TCATCATTGG
7681 AAAACGTTCT TCGGGGCGAA AACTCTCAAG GATCTTACCG CTGTTGAGAT CCAGTTCGAT
7741 GTAACCCACT CGTGCACCCA ACTGATCTTC AGCATCTTTT ACTTTCACCA GCGTTTCTGG
7801 GTGAGCAAAA ACAGGAAGGC AAAATGCCGC AAAAAAGGGA ATAAGGGCGA CACGGAAATG
7861 TTGAATACTC ATACTCTTCC TTTTTCAATA TTATTGAAGC ATTTATCAGG GTTATTGTCT
7921 CATGAGCGGA TACATATTTG AATGTATTTA GAAAAATAAA CAAATAGGGG TTCCGCGCAC
7981 ATTTCCCCGA AAAGTGCCAC CTGACGTCTA AGAAACCATT ATTATCATGA CATTAACCTA
8041 TAAAAATAGG CGTATCACGA GGCCCTTTCG TC
```

VECTORS FOR PROTEIN MANUFACTURE

CROSS REFERENCE TO RELATED APPLICATIONS

This application is a U.S. 371 national phase entry of International Patent Application No. PCT/US2019/064423, filed Dec. 4, 2019, which claims priority to U.S. Provisional Application No. 62/775,194, filed Dec. 4, 2018, the entire contents of which are incorporated herein by reference.

FIELD OF THE INVENTION

The present invention relates to vectors and their use to develop host cell lines for production of a protein of interest, and in particular to vectors which utilize a weak promoter to drive a selectable marker.

BACKGROUND OF THE INVENTION

Therapeutic protein drugs are an important class of medicines serving patients most in need of novel therapies. Recently approved recombinant protein therapeutics have been developed to treat a wide variety of clinical indications, including cancers, autoimmunity/inflammation, exposure to infectious agents, and genetic disorders. The latest advances in protein-engineering technologies have allowed drug developers and manufacturers to fine-tune and exploit desirable functional characteristics of proteins of interest while maintaining (and in some cases enhancing) product safety or efficacy or both.

The manufacturing and production of therapeutic proteins are highly complex processes. For example, a typical protein drug may include in excess of 5,000 critical process steps, many times greater than the number required for manufacturing a small-molecule drug.

Similarly, protein therapeutics, which include monoclonal antibodies as well as large or fusion proteins, can be orders-of-magnitude larger in size than small-molecule drugs, having molecular weights exceeding 100 kDa. In addition, protein therapeutics exhibit complex secondary and tertiary structures that must be maintained. Protein therapeutics cannot be completely synthesized by chemical processes and have to be manufactured in living cells or organisms: consequently, the choices of the cell line, species origin, and culture conditions all affect the final product characteristics. Moreover, most biologically active proteins require post-translational modifications that can be compromised when heterologous expression systems are used. Additionally, as the products are synthesized by cells or organisms, complex purification processes are involved. Furthermore, viral clearance processes such as removal of virus particles by using filters or resins, as well as inactivation steps by using low pH or detergents, are implemented to prevent the serious safety issue of viral contamination of protein drug substances. Given the complexity of therapeutic proteins with respect to their large molecular size, post-translational modifications, and the variety of biological materials involved in their manufacturing process, the ability to enhance particular functional attributes while maintaining product safety and efficacy achieved through protein-engineering strategies is highly desirable.

While the integration of novel strategies and approaches to modify protein drug products is not a trivial matter, the potential therapeutic advantages have driven the increased use of such strategies during drug development. A number of protein-engineering platform technologies are currently in use to increase the circulating half-life, targeting, and functionality of novel therapeutic protein drugs as well as to increase production yield and product purity. For example, protein conjugation and derivatization approaches, including Fc-fusion, albumin-fusion, and PEGylation, are currently being used to extend a drug's circulating half-life.

The production of protein pharmaceutical (biologics) is expensive and time consuming. What is needed in the art are more efficient tools and processes for producing this important class of drugs.

SUMMARY OF THE INVENTION

The present invention relates to vectors and their use to develop host cell lines for production of a protein of interest, and in particular to vectors which utilize a weak promoter to drive a selectable marker.

Accordingly, in some preferred embodiments, the present invention provides vector(s) for expression of a protein of interest comprising a nucleic acid sequence encoding a selectable marker in operable association with a first promoter sequence that has been altered to reduce promoter activity as compared to a non-altered or wild-type version of the first promoter sequence and a nucleic acid sequence encoding the protein of interest operably linked to a second promoter sequence.

In some preferred embodiments, the first promoter sequence that has been altered to reduce promoter activity as compared to a non-altered or wild-type version of the first promoter sequence is a viral Self-Inactivating (SIN) Long Terminal Repeat (LTR) promoter sequence. In some preferred embodiments, the SIN LTR promoter sequence is at least 95% identical to SEQ ID NO:3. In some preferred embodiments, the SIN LTR promoter sequence is SEQ ID NO:3.

In some preferred embodiments, the selectable marker is Glutamine Synthetase (GS). In some preferred embodiments, the selectable marker is Dihydrofolate Reductase (DHFR).

In some embodiments, the vector comprises a single poly A signal sequence in operable association with the selectable marker and the nucleic acid encoding a protein of interest. In other embodiments, the vector comprises a first poly A signal sequence in operable association with the selectable marker and a second poly A signal sequence in operable association the nucleic acid encoding a protein of interest.

In some preferred embodiments, the protein of interest is selected from the group consisting of an Fc-fusion protein, an enzyme, an albumin fusion, a growth factor, a protein receptor, a single chain antibody (scFv), a single chain-Fc (scFv-Fc), a diabody, and minibody (scFv-CH3), Fab, single chain Fab (scFab), an immunoglobulin heavy chain, and an immunoglobulin light chain. In some preferred embodiments, the protein of interest is an Fc-fusion protein.

In some embodiments, the vector is a plasmid. In some preferred embodiments, the vector is a viral vector. In some preferred embodiments, the vector is a retroviral vector. In some preferred embodiments, the vector is a lentiviral vector.

In some preferred embodiments, the present invention provides a host cell(s) comprising a vector as described above. In some preferred embodiments, the host cell line is a GS knockout cell line. In some preferred embodiments, the host cell line is a DHFR knockout cell line. In some preferred embodiments, the host cell line is Chinese Hamster Ovary (CHO) cell line. In some preferred embodiments, the host cell line is a HEK 293 or CAP cell line In some preferred embodiments, the host cell comprises from about 1, 20, 50 to 1000 copies of the vector. In some preferred embodiments, the host cell comprises from about 10 to 200 copies of the vector. In some preferred embodiments, the host cell comprises from about 10 to 100 copies of the vector. In some preferred embodiments, the host cell comprises from about 20 to 100 copies of the vector.

In some preferred embodiments, the host cell further comprises at least a second vector that encodes and allows for expression of a second protein of interest, and wherein said second vector does not include a selectable marker. In some preferred embodiments, the host cell further comprises at least a second vector that encodes and allows for expression of a second protein of interest, and wherein said second vector includes a selectable marker that is different from the selectable marker in the first vector. In some preferred embodiments, the first protein of interest in the first vector is one of an immunoglobulin heavy or light chain and the second protein in the second vector is the other of an immunoglobulin heavy or light chain. In some preferred embodiments, the first protein of interest is an immunoglobulin heavy chain and the second protein of interest is an immunoglobulin light chain. In some preferred embodiments, the host cell comprises from about 1, 20, 50 or 100 to 1000 copies of the second vector. In some preferred embodiments, the host cell comprises from about 10 to 200 copies of the second vector. In some preferred embodiments, the host cell comprises from about 10 to 100 copies of the second vector. In some preferred embodiments, the host cell comprises from about 20 to 100 copies of the second vector.

In some preferred embodiments, the present invention provides a host cell culture comprising host cells as described above. In some preferred embodiments, the culture produces from 1 to 50 grams/liter/day of the protein of interest. In some preferred embodiments, the culture produces from 2 to 10 grams/liter/day of the protein of interest.

In some preferred embodiments, the present invention provides a process for producing a protein of interest comprising culturing host cells as described above and purifying the protein of interest from the host cell culture.

In some preferred embodiments, the present invention provides an infectious retroviral particle comprising the following elements in 5' to 3' order: 1) a 5' LTR; 2) a retroviral packaging region; 3) a nucleic acid encoding a selectable marker; 4) an internal promoter; 5) a nucleic acid sequence encoding a protein of interest that is operably linked to the internal promoter; and 6) a SIN 3' LTR. In some preferred embodiments, the 5'LTR is an MoMuSV LTR or a SIN LTR. In some embodiments, the 3' LTR comprises a poly A signal sequence. In some embodiments, the packaging region comprises a plurality of potential translation start sites. In some preferred embodiments, the selectable marker is GS. In some preferred embodiments, the internal promoter is a CMV promoter. In some embodiments, the particle comprises a single poly A signal sequence downstream of the nucleic acid encoding the protein of interest. In some embodiments, the particles comprises a first poly A signal sequence in operable association with the selectable marker and a second poly A signal sequence in operable association with the nucleic acid encoding the gene of interest.

Further embodiments provide a plasmid comprising the following elements in 5' to 3" order: 1) a 5' LTR (e.g., SIN LTR); 2) a packaging region; 3) a selectable marker (e.g., GS); 4) an internal promoter (e.g., a CMV promoter); 5) a nucleic acid sequence encoding a protein of interest that is operably linked to the internal promoter; and 6) a poly A signal sequence. In some embodiments, the plasmid comprises a single poly A signal sequence downstream of the nucleic acid encoding the protein of interest.

Additional embodiments provide a system, comprising: a) a first vector comprising a nucleic acid sequence encoding a selectable marker in operable association with a first promoter sequence that has been altered to reduce promoter activity as compared to a non-altered or wild-type version of the first promoter sequence and a nucleic acid sequence encoding a first protein of interest operably linked to a second promoter sequence; and b) a second vector comprising a nucleic acid sequence encoding a second protein of interest operably linked to a promoter sequence, and wherein the second vector does not include a selectable marker.

In some preferred embodiments, the present invention provides a process for producing a protein of interest comprising: transducing or transfecting a host cell or cells with an infectious retroviral particle, plasmid, or vector system as described above, developing a host cell line that expresses the protein of interest from the host cell or cells; culturing the host cells under conditions such that the protein of interested is produced by the host cell line; and purifying the protein of interest from the host cell culture.

In some preferred embodiments, the present invention provides an infectious retroviral particle or plasmid as described above for use in transducing a host cell or cells for production of a protein of interest.

DESCRIPTION OF THE FIGURES

FIG. 3. Sequence of full length MMLV construct (SEQ ID NO:1).

FIG. 4. Sequence of SIN MMLV LTR construct (SEQ ID NO:2).

FIG. 7. SIN LTR sequence (SEQ ID NO:3).

FIG. 9. Sequence of proviral plasmid construct (SEQ ID NO: 4).

DEFINITIONS

Figure 1:
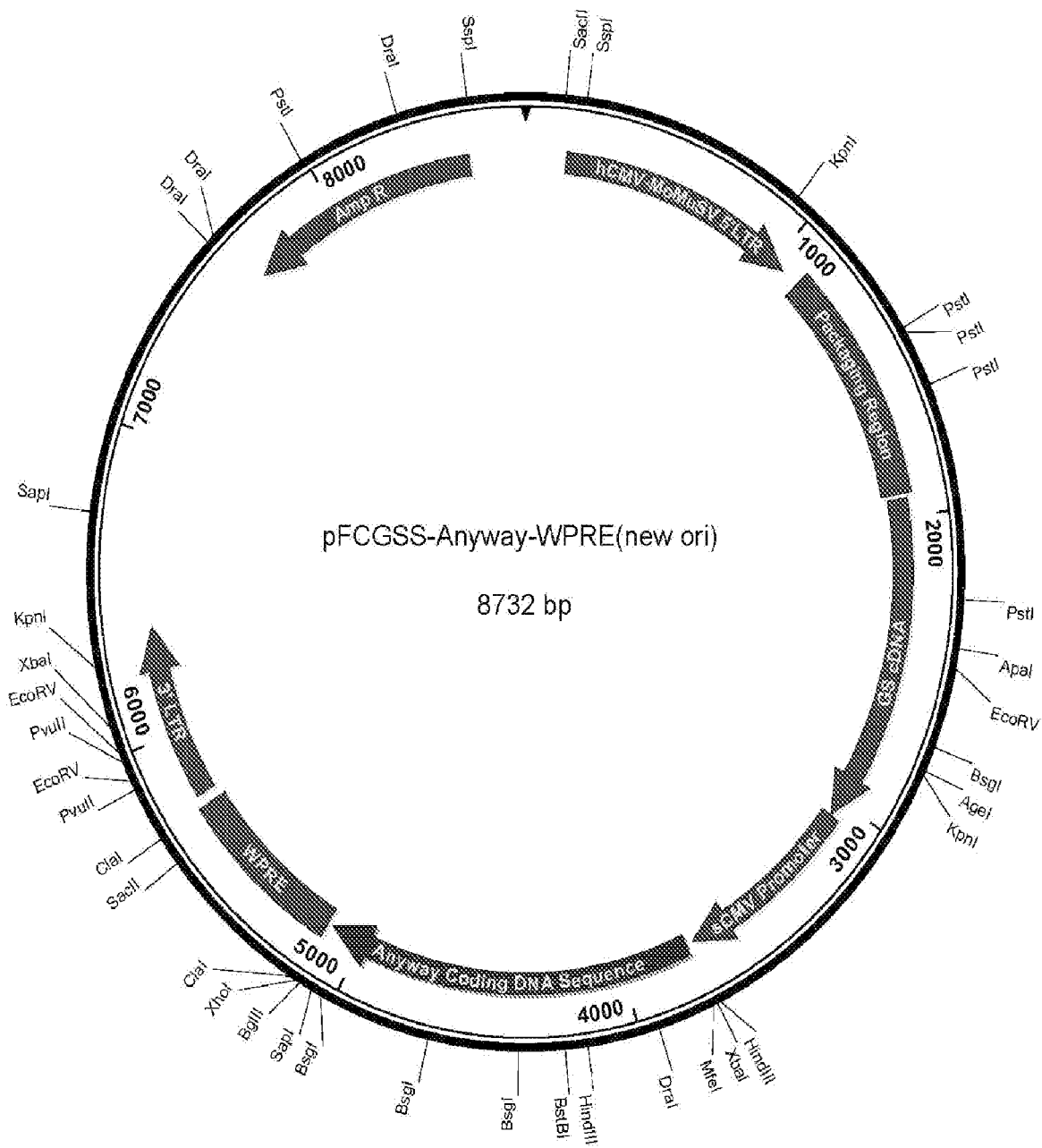
FIG. 1. Map of full length MMLV construct.

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chomosomes) of an organism.

The term "nucleotide sequence of interest" refers to any nucleotide sequence (e.g . . . . RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

As used herein, the term "altered," when used in reference to a promoter, refers to promoters that have an altered nucleic acid sequence as compared to a reference wild type sequence. For example, the sequence promoter may be altered by deleting certain promoter and/or enhancer elements.

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11:287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "homology" and "percent identity" when used in relation to nucleic acids refers to a degree of complementarity. There may be partial homology (i.e., partial identity) or complete homology (i.e., complete identity). A partially complementary sequence is one that at least partially inhibits a completely complementary sequence from hybridizing to a target nucleic acid sequence and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe (i.e., an oligonucleotide which is capable of hybridizing to another oligonucleotide of interest) will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity or other protein that confers the ability to grow in medium lacking what would otherwise be an essential nutrient; in addition, a selectable marker may confer resistance to an antibiotic or drug upon the cell in which the selectable marker is expressed.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMLV), Moloney murine sarcoma virus (MoMSV), and Mouse mammary tumor virus (MMTV), Spumavirinae, amd Lentivirinae (e.g., Human immunodeficiency virus, Simian immunodeficiency virus, Equine infection anemia virus, and Caprine arthritis-encephalitis virus; See. e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting their viral infectious process. Foreign or heterologous genes cloned (i.e., inserted using molecular biological techniques) into the retroviral genome can be delivered efficiently to host cells that are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola) that are associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

The term "heterologous membrane-associated protein" refers to a membrane-associated protein which is derived from a virus that is not a member of the same viral class or family as that from which the nucleocapsid protein of the vector particle is derived. "Viral class or family" refers to the taxonomic rank of class or family, as assigned by the International Committee on Taxonomy of Viruses.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See. e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein, the term "transposon" refers to transposable elements (e.g., Tn5, Tn7, and Tn10) that can move or transpose from one position to another in a genome. In general, the transposition is controlled by a transposase. The term "transposon vector," as used herein, refers to a vector encoding a nucleic acid of interest flanked by the terminal ends of transposon. Examples of transposon vectors include, but are not limited to, those described in U.S. Pat. Nos. 6,027,722; 5,958,775; 5,968,785; 5,965,443; and 5,719,055, all of which are incorporated herein by reference.

As used herein, the term "adeno-associated virus (AAV) vector" refers to a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences.

AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence. A "recombinant AAV vector plasmid" refers to one type of recombinant AAV vector wherein the vector comprises a plasmid. As with AAV vectors in general, 5' and 3' ITRs flank the selected heterologous nucleotide sequence.

AAV vectors can also include transcription sequences such as polyadenylation sites, as well as selectable markers or reporter genes, enhancer sequences, and other control elements that allow for the induction of transcription. Such control elements are described above.

As used herein, the term "AAV virion" refers to a complete virus particle. An AAV virion may be a wild type AAV virus particle (comprising a linear, single-stranded AAV nucleic acid genome associated with an AAV capsid, i.e., a protein coat), or a recombinant AAV virus particle (described below). In this regard, single-stranded AAV nucleic acid molecules (either the sense/coding strand or the antisense/anticoding strand as those terms are generally defined) can be packaged into an AAV virion; both the sense and the antisense strands are equally infectious.

As used herein, the term "recombinant AAV virion" or "rAAV" is defined as an infectious, replication-defective virus composed of an AAV protein shell encapsidating (i.e., surrounding with a protein coat) a heterologous nucleotide sequence, which in turn is flanked 5' and 3' by AAV ITRs. A number of techniques for constructing recombinant AAV virions are known in the art (See. e.g., U.S. Pat. No. 5,173,414; WO 92/01070; WO 93/03769; Lebkowski et al., Molec. Cell. Biol. 8:3988-3996 [1988]; Vincent et al., Vaccines 90 (Cold Spring Harbor Laboratory Press); Carter, Current Opinion in Biotechnology 3:533-539 [1992]; Muzyczka, Current Topics in Microbiol. and Immunol. 158:97-129 [1992]; Kotin, Human Gene Therapy 5:793-801 [1994]; Shelling and Smith, Gene Therapy 1:165-169 [1994]; and Zhou et al., J. Exp. Med. 179:1867-1875 [1994], all of which are incorporated herein by reference).

Suitable nucleotide sequences for use in AAV vectors (and, indeed, any of the vectors described herein) include any functionally relevant nucleotide sequence. Thus, the AAV vectors of the present invention can comprise any desired gene that encodes a protein that is defective or missing from a target cell genome or that encodes a non-native protein having a desired biological or therapeutic effect (e.g., an antiviral function), or the sequence can correspond to a molecule having an antisense or ribozyme function. Suitable genes include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. A number of antisense oligonucleotides (e.g., short oligonucleotides complementary to sequences around the translational initiation site (AUG codon) of an mRNA) that are useful in antisense therapy for cancer and for viral diseases have been described in the art. (See. e.g., Han et al., Proc. Natl. Acad. Sci. USA 88:4313-4317 [1991]; Uhlmann et al., Chem. Rev. 90:543-584 [1990]; Helene et al., Biochim. Biophys. Acta. 1049:99-125 [1990]; Agarwal et al., Proc. Natl. Acad. Sci. USA 85:7079-7083 [1989]; and Heikkila et al., Nature 328:445-449 [1987]). For a discussion of suitable ribozymes, see. e.g., Cech et al. (1992) J. Biol. Chem. 267: 17479-17482 and U.S. Pat. No. 5,225,347, incorporated herein by reference.

As used herein, the term "purified" refers to molecules, either nucleic or amino acid sequences, that are removed from their normal environment, isolated or separated. An "isolated nucleic acid sequence" is therefore a purified nucleic acid sequence. "Substantially purified" molecules are at least 60% free, preferably at least 75% free, and more preferably at least 90% free from other components with which they are normally associated.

DETAILED DESCRIPTION OF THE INVENTION

The present invention relates to vectors and their use to develop host cell lines for production of a protein of interest, and in particular to vectors which utilize a weak promoter to drive a selectable marker.

In some preferred embodiments, the expression systems of the present invention utilize an expression vector that includes a nucleic acid sequence encoding a protein of interest (i.e., a therapeutic protein or other protein that is desired to be produced) in operable association with additional nucleic acid sequences that serve various functions. Thus, for example, the nucleic acid sequence of interest may be included in any one of a variety of expression vectors for expressing a polypeptide. In some embodiments of the present invention, vectors include, but are not limited to, retroviral vectors, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host. In some preferred embodiments, the vectors are retroviral vectors as described in U.S. Pat. Nos. 6,852,510 and 7,332,333 and U.S. pat. Publ. Nos. 200402335173 and 20030224415, all of which are incorporated herein by references in their entirety. In some especially preferred embodiments, the vectors are pseudotyped retroviral vectors. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In some preferred embodiments, the vectors are retroviral vectors. The organization of the genomes of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector which contains the sequences necessary for the efficient expression of the gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (–PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotropic, amphotropic or xenotropic envelope gene products.

Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles, which contain the membrane-associated protein expressed by the transfected packaging cell line; these viral particles, which contain viral genomic RNA derived from one virus encapsidated by the envelope proteins of another virus are said to be pseudotyped virus particles.

The retroviral vectors of the present invention can be further modified to include additional regulatory sequences. As described above, the retroviral vectors of the present invention include the following elements in operable association: a) a 5' LTR; b) a packaging signal; c) a 3' LTR and d) a nucleic acid encoding a protein of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter (human or simian), and the thymidine kinase promoter.

In other embodiments of the present invention, where secretion of the protein of interest is desired, the vectors are modified by including a signal peptide sequence in operable association with the protein of interest. The sequences of several suitable signal peptides are known to those in the art, including, but not limited to, those derived from tissue plasminogen activator, human growth hormone, lactoferrin, alpha-casein, and alpha-lactalbumin.

In other embodiments of the present invention, the vectors are modified by incorporating an RNA export element (See, e.g., U.S. Pat. Nos. 5,914,267; 6,136,597; and 5,686,120; and WO99/14310, all of which are incorporated herein by reference) either 3' or 5' to the nucleic acid sequence encoding the protein of interest. It is contemplated that the use of RNA export elements allows high levels of expression of the protein of interest without incorporating splice signals or introns in the nucleic acid sequence encoding the protein of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the same promoter.

The most commonly used recombinant retroviral vectors are derived from the amphotropic Moloney murine leukemia virus (MoMLV) (See e.g., Miller and Baltimore Mol. Cell. Biol. 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

In some preferred embodiments, the retroviral vectors are pseudotyped, and for example utilize the G protein of VSV as the membrane associated protein. Unlike retroviral envelope proteins that bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention is not limited to the use of the VSV G protein when a viral G protein is employed as the heterologous membrane-associated protein within a viral particle (See, e.g., U.S. Pat. No. 5,512,421, which is incorporated herein by reference). The G proteins of viruses in the Vesiculovirus genera other than VSV, such as the Piry and Chandipura viruses, that are highly homologous to the VSV G protein and, like the VSV G protein, contain covalently linked palmitic acid (Brun et al. Interviol. 38:274 [1995] and Masters et al., Virol. 171:285 (1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69:1444 [1995]). Viral particles may be pseudotyped using either the Piry, Chandipura or Mokola G protein as described in Example 2, with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

In some preferred embodiments, the vectors are lentiviral vectors. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described above for retroviral vectors.

In some preferred embodiments, the vectors are adeno-associated virus (AAV) vectors. AAV is a human DNA parvovirus, which belongs to the genus Dependovirus. The AAV genome is composed of a linear, single-stranded DNA molecule that contains approximately 4680 bases. The genome includes inverted terminal repeats (ITRs) at each end that function in cis as origins of DNA replication and as packaging signals for the virus. The internal nonrepeated portion of the genome includes two large open reading frames, known as the AAV rep and cap regions, respectively. These regions code for the viral proteins involved in replication and packaging of the virion. A family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3 (for a detailed description of the AAV genome, see e.g., Muzyczka, Current Topics Microbiol. Immunol. 158:97-129 [1992]: Kotin, Human Gene Therapy 5:793-801 [1994])

AAV requires coinfection with an unrelated helper virus, such as adenovirus, a herpesvirus or vaccinia, in order for a productive infection to occur. In the absence of such coinfection, AAV establishes a latent state by insertion of its genome into a host cell chromosome. Subsequent infection by a helper virus rescues the integrated copy, which can then replicate to produce infectious viral progeny. Unlike the non-pseudotyped retroviruses, AAV has a wide host range and is able to replicate in cells from any species so long as there is coinfection with a helper virus that will also multiply in that species. Thus, for example, human AAV will replicate in canine cells coinfected with a canine adenovirus. Furthermore, unlike the retroviruses, AAV is not associated with any human or animal disease, does not appear to alter the biological properties of the host cell upon integration and is able to integrate into nondividing cells. It has also recently been found that AAV is capable of site-specific integration into a host cell genome.

In light of the above-described properties, a number of recombinant AAV vectors have been developed for gene delivery (See, e.g., U.S. Pat. Nos. 5,173,414; 5,139,941; WO 92/01070 and WO 93/03769, both of which are incorporated herein by reference; Lebkowski et al., Molec. Cell. Biol. 8:3988-3996 [1988]; Carter, Current Opinion in Biotechnology 3:533-539 [1992]; Muzyczka, Current Topics in Microbiol. and Immunol. 158:97-129 [1992]; Kotin, (1994) Human Gene Therapy 5:793-801; Shelling and Smith, Gene Therapy 1:165-169 [1994]; and Zhou et al., J. Exp. Med. 179:1867-1875 [1994]).

Recombinant AAV virions can be produced in a suitable host cell that has been transfected with both an AAV helper plasmid and an AAV vector. An AAV helper plasmid generally includes AAV rep and cap coding regions, but lacks AAV ITRs. Accordingly, the helper plasmid can neither replicate nor package itself. An AAV vector generally includes a selected gene of interest bounded by AAV ITRs that provide for viral replication and packaging functions. Both the helper plasmid and the AAV vector bearing the selected gene are introduced into a suitable host cell by transient transfection. The transfected cell is then infected with a helper virus, such as an adenovirus, which transactivates the AAV promoters present on the helper plasmid that direct the transcription and translation of AAV rep and cap regions. Recombinant AAV virions harboring the selected gene are formed and can be purified from the preparation. Once the AAV vectors are produced, they may be used to transfect (See, e.g., U.S. Pat. No. 5,843,742, herein incorporated by reference) host cells at the desired multiplicity of infection to produce high copy number host cells. As will be understood by those skilled in the art, the AAV vectors may also be modified as described above to contain various regulatory sequences (e.g., signal peptide sequences, RNA export elements, and IRES's).

In some preferred embodiments, the vectors are transposon-based vectors. Transposons are mobile genetic elements that can move or transpose from one location another in the genome. Transposition within the genome is controlled by a transposase enzyme that is encoded by the transposon. Many examples of transposons are known in the art, including, but not limited to, Tn5 (See e.g., de la Cruz et al., J. Bact. 175: 6932-38 [1993], Tn7 (See e.g., Craig, Curr. Topics Microbiol. Immunol. 204: 27-48 [1996]), and Tn10 (See e.g., Morisato and Kleckner, Cell 51:101-111 [1987]). The ability of transposons to integrate into genomes has been utilized to create transposon vectors (See, e.g., U.S. Pat. Nos. 5,719, 055; 5,968,785; 5,958,775; and 6,027,722; all of which are incorporated herein by reference.) Because transposons are not infectious, transposon vectors are introduced into host cells via methods known in the art (e.g., electroporation, lipofection, or microinjection). Therefore, the ratio of transposon vectors to host cells may be adjusted to provide the desired multiplicity of infection to produce the high copy number host cells of the present invention.

Transposon vectors suitable for use in the present invention generally comprise a nucleic acid encoding a protein of interest interposed between two transposon insertion sequences. Some vectors also comprise a nucleic acid sequence encoding a transposase enzyme. In these vectors, one of the insertion sequences is positioned between the transposase enzyme and the nucleic acid encoding the protein of interest so that it is not incorporated into the genome of the host cell during recombination. Alternatively, the transposase enzyme may be provided by a suitable method (e.g., lipofection or microinjection). As will be understood by those skilled in the art, the transposon vectors may also be modified as described above to contain various regulatory sequences (e.g., signal peptide sequences, RNA export elements, and IRES's).

In some preferred embodiments, the vectors include a selectable marker. Suitable selectable markers include but are not limited to glutamine synthetase (GS), dihydrofolate reductase (DHFR) and the like. These genes are described in U.S. Pat. Nos. 5,770,359; 5,827,739; 4,399,216; 4,634,665; 5,149,636; and 6,455,275; all of which are incorporated herein by reference. In some particularly preferred embodiments, the selectable marker is GS and has a sequence that shares at least 80%, 90%, 95%, 99% or 100% identity with the sequence from positions 1789 to 2910 of SEQ ID NO:2. In some preferred embodiments, the selectable marker that is utilized is compatible with a host cell line that is deficient in the production of the enzyme encoded by the selectable marker nucleic acid sequence. Suitable host cell lines are described in more detail below. In other embodiments, the selectable marker is an antibiotic resistance marker, i.e., a gene that produces a protein that provides cells expressing this protein with resistance to an antibiotic. Suitable antibiotic resistance markers include genes that provide resistance to neomycin (neomycin resistance gene (neo)), hygromycin (hygromycin B phosphotransferase gene), puromycin (puromycin N-acetyl-transferase), and the like.

In some embodiments, the nucleic acid sequence encoding the selectable marker is operably linked to a promoter sequence. In some particularly preferred embodiments, the promoter sequence has been altered, for example by mutation, to have reduced promoter activity as compared to an unaltered version of the promoter. These promoters may be described as weak promoters in that the expression of the gene linked to the promoter occurs at a low level as opposed to a high level. Genes regulated by strong promoters yield more mRNA and therefore more product protein than genes regulated by weak promoters. Thus, the instant invention preferably utilizes a promoter for the selectable marker that has been altered to yield less mRNA that the comparable unaltered promoter.

In some preferred embodiments, the promoter that is operably linked to the selectable marker is a long terminal repeat (LTR) from a retrovirus or lentivirus. In some particularly preferred embodiments, the promoter is an LTR that has been altered by removing either all or a portion of the U3 region of the LTR. In some embodiments, the promoter that is operably linked to the selectable marker is a self-inactivating (SIN) LTR. Suitable SIN LTRs are known in the art. In some preferred embodiments, the SIN LTRs of the present invention preferably have at least 80%, 90%, 95%, 99% or 100% identity to SEQ ID NO:3 and the SIN LTR most preferably has therein a deletion in the U3 region that reduces promoter activity as compared to promoter activity when there is no deletion in the U3 region.

Figure 2:
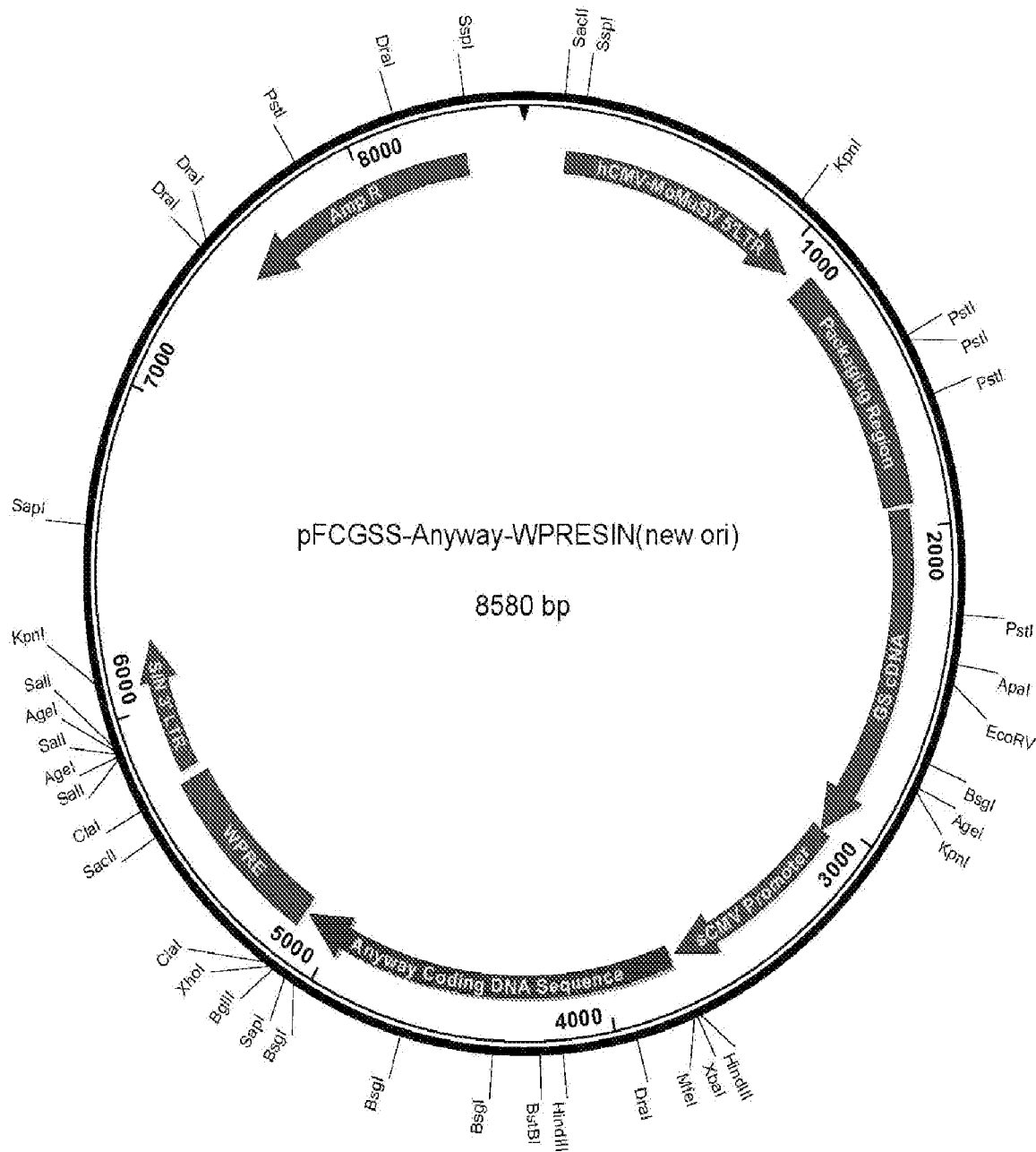
FIG. 2. Map of SIN MMLV LTR construct.

It will be understood that where the vector is a retroviral vector, the vector is constructed so that the SIN LTR is the 3' LTR of the retroviral vector sequence. Due to the fact that the U3 deletion is copied to the 5' and 3' LTRs during reverse transcription, integrated SIN vectors contain only LTRs with U3 deleted. A map of an exemplary retroviral vector of the instant invention is provided as FIG. 2. As can be seen, the vector contains a SIN 3' LTR. When reverse transcribed, the hCMV-MOMuSV LTR depicted in the vector map is replaced by the SIN 3' LTR depicted in the vector map so that when the vector is integrated into the host cell chromosome the SIN LTR is operably linked to and drives the expression of the depicted GS cDNA.

In certain preferred embodiments of the present invention, the nucleic acid sequence encoding the protein of interest in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses.

As mentioned above, an exemplary map of a vector of the present invention is provided in FIG. 3 and corresponds to SEQ ID NO:2. In some preferred embodiments, the vectors comprise the following elements in 5' to 3' order:
  5' LTR (exemplified by the hCMV-MoMuSV LTR)
  a retroviral packaging region
  a nucleic acid encoding a selectable marker (exemplified by a GS cDNA)
  an internal promoter (exemplified by the simian CMV (sCMV) promoter
  a nucleic acid sequence encoding the protein of interest (exemplified by the "anyway" sequence) that is operably linked to the internal promoter
  a WPRE sequence
  a SIN 3' LTR.

In some embodiments, the vector is a plasmid comprising the following elements in 5' to 3' order: 1) a 5' LTR (e.g., SIN LTR); 2) a packaging region; 3) a selectable marker (e.g., GS); 4) an internal promoter (e.g., a CMV promoter); and 5) a nucleic acid sequence encoding a protein of interest that is operably linked to the internal promoter.

In some embodiments, vectors comprise a single poly A signal sequence downstream of the nucleic acid encoding the protein of interest. For example, in some embodiments, the vector comprises the following components in 5' to 3' order: Promoter (e.g., SIN)—selectable marker-stop codon-promoter (e.g., CMV)—protein of interest—stop codon-poly A.

In some embodiments, the present invention provides host cells and host cell culture wherein the host cells express the protein of interest from the vectors described above. In preferred embodiment, the host cells a mammalian host cells. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular protein of interest into the culture medium. Examples of suitable mammalian host cells include, but are not limited to Chinese hamster ovary cells (CHO-KI, ATCC CCI-61); bovine mammary epithelial cells (ATCC CRL 10274; bovine mammary epithelial cells); monkey kidney CVI line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); CAP (CEVEC's Amniocyte Production) cells; and a human hepatoma line (Hep G2).

In some particularly preferred embodiments, the host cells are modified so that they are deficient, or are naturally deficient, in an enzyme activity that is required for growth or survival of the cells in the presence of a selection agent and which is provided by the selectable marker. For example, Chinese Hamster Ovary (CHO) cells have been modified to be deficient for GS. In some preferred embodiments where vector includes a GS selectable marker, the host cell line is deficient in GS. In some particularly preferred embodiments, the GS deficient host cell line is the CHOZN™ GS$^{-/-}$ cell line available from Merck KGaA. In other embodiments, where the selectable marker is, for example, DHFR, the cell line may preferably be deficient for DHFR activity (i.e., DHFR$^-$). Suitable DHFR-cell lines include but are not limited to CHO-DG44 and derivatives thereof.

The vectors may be introduced in the host cells by any suitable means. In some preferred embodiments, vectors (e.g., retroviral vectors) encoding a protein of interest have been produced, they may be used to transfect or transduce host cells. Preferably, host cells are transfected or transduced with integrating vectors at a multiplicity of infection sufficient to result in the integration of at least 1, and preferably at least 2 or more retroviral vectors. In some embodiments, multiplicities of infection of from 10 to 1,000,000 may be utilized, so that the genomes of the infected host cells contain from 2 to 1000 copies of the integrated vectors, preferably from 5 to 1000 copies of the integrated vectors, and most preferably from 20 to 500 copies of the integrated vectors. In other embodiments, a multiplicity of infection of from 10 to 10,000 is utilized. When non-pseudotyped retroviral vectors are utilized for infection, the host cells are incubated with the culture medium from the retroviral producer cells containing the desired titer (i.e., colony forming units, CFUs) of infectious vectors. When pseudotyped retroviral vectors are utilized, the vectors are concentrated to the appropriate titer by ultracentrifugation and then added to the host cell culture. Alternatively, the concentrated vectors can be diluted in a culture medium appropriate for the cell type. Additionally, when expression of more than one protein of interest by the host cell is desired, the host cells can be transfected with multiple vectors each containing a nucleic acid encoding a different protein of interest.

In each case, the host cells are exposed to medium containing the infectious retroviral vectors for a sufficient period of time to allow infection and subsequent integration of the vectors. In general, the amount of medium used to overlay the cells should be kept to as small a volume as possible so as to encourage the maximum amount of integration events per cell. As a general guideline, the number of colony forming units (cfu) per milliliter should be about $10^5$ to $10^7$ cfu/ml, depending upon the number of integration events desired.

In some embodiments, after transfection or transduction, the cells are allowed to multiply, and are then trypsinized and replated. Individual colonies are then selected to provide clonally selected cell lines. In still further embodiments, the clonally selected cell lines are screened by Southern blotting or PCR assays to verify that the desired number of integration events has occurred. It is also contemplated that clonal selection allows the identification of superior protein producing cell lines. In other embodiments, the cells are not clonally selected following transfection.

In some embodiments, the host cells are transfected with vectors encoding different proteins of interest. The vectors encoding different proteins of interest can be used to transfect the cells at the same time (e.g., the host cells are exposed to a solution containing vectors encoding different proteins of interest) or the transfection can be serial (e.g., the host cells are first transfected with a vector encoding a first protein of interest, a period of time is allowed to pass, and the host cells are then transfected with a vector encoding a second protein of interest). In some preferred embodiments, the host cells are transfected with an integrating vector encoding a first protein of interest, high expressing cell lines containing multiple integrated copies of the integrating vector are selected (e.g., clonally selected), and the selected cell line is transfected with an integrating vector encoding a second protein of interest. This process may be repeated to introduce multiple proteins of interest. In some embodiments, the multiplicities of infection may be manipulated (e.g., increased or decreased) to increase or decrease the expression of the protein of interest. Likewise, the different promoters may be utilized to vary the expression of the proteins of interest. It is contemplated that these transfection methods can be used to construct host cell lines containing an entire exogenous metabolic pathway or to provide host cells with an increased capability to process proteins (e.g., the host cells can be provided with enzymes necessary for post-translational modification).

In still further embodiments, cell lines are serially transfected with vectors encoding the same gene. In some preferred embodiments, the host cells are transfected (e.g., at an MOI of about 10 to 1,000,000, preferably 100 to 10,000) with an integrating vector encoding a protein of interest, cell lines containing single or multiple integrated copies of the integrating vector or expressing high levels of the desired protein are selected (e.g., clonally selected), and the selected cell line is retransfected with the vector (e.g., at an MOI of about 10 to 1,000,0000; preferably 100 to 10,000). In some embodiments, cell lines comprising at least two integrated copies of the vector are identified and selected. This process may be repeated multiple times until the desired level of protein expression is obtained and may also be repeated to introduce vectors encoding multiple proteins of interest. Unexpectedly, serial transfection with the same gene results in increases in protein production from the resulting cells that are not merely additive.

The present invention contemplates a variety of serial transfection procedures. In some embodiments, where retroviral vectors are utilized, serial transduction procedures are provided. In preferred embodiments, serial transduction is carried out on a pool of cells. In these embodiments, an initial pool of host cells is contacted with retroviral vectors, preferably at a multiplicity of infection ranging from about 0.5 to about 1000 vectors/host cell. The cells are then cultured for several days in an appropriate medium (e.g., with a selection agent). An aliquot of the cells in then taken to determine the number of integrated vectors and to freeze for future possible use. The remaining cells are then recontacted with retroviral vectors, again preferably at a multiplicity of infection ranging from about 0.5 to about 1000 vectors/host cell. This process is repeated until cells with a desired number of integrated vectors are obtained. For example, the process can be repeated up to 10 to 20 or more times. In some embodiments, cells can be clonally selected after any particular transduction step if so desired, however, utilizing a pool of cells in the absence of transduction results in a decreased time to the desired integrated vector copy number.

In some embodiments of the present invention, following transformation of a suitable host strain and growth of the host strain to an appropriate cell density in media, the protein of interest is secreted during culture of the host cells. In some preferred embodiments where amplifiable markers are utilized, it is contemplated that culture of transduced host cells in a medium comprising an inhibitor of the gene. Suitable inhibitors include, but are not limited to methotrexate for inhibition of DHFR and methionine sulphoximine (Msx) or phosphinothricin for inhibition of GS. It is contemplated that as concentrations of these inhibitors are increased in a cell culture system, cells with higher copy numbers of the amplifiable marker (and thus the genes or genes of interest) or which contain higher-producing insertions are selected.

Accordingly, the host cells containing vectors as described above are cultured according to methods known in the art. Suitable culture conditions for mammalian cells are well known in the art (See e.g., J. Immunol. Methods (1983) 56:221-234 [1983], Animal Cell Culture: A Practical Approach 2nd Ed., Rickwood, D. and Hames, B. D., eds. Oxford University Press, New York [1992]).

The host cell cultures of the present invention are prepared in a media suitable for the particular cell being cultured. Commercially available media such as ActiPro media (HyClone), ExCell Advanced Fed Batch Medium (SAFC), Ham's F10 (Sigma, St. Louis, MO), Minimal Essential Medium (MEM, Sigma), RPMI-1640 (Sigma), and Dulbecco's Modified Eagle's Medium (DMEM, Sigma) are exemplary nutrient solutions. Suitable media are also described in U.S. Pat. Nos. 4,767,704; 4,657,866; 4,927,762; 5,122,469; 4,560,655; and WO 90/03430 and WO 87/00195; the disclosures of which are herein incorporated by reference. Any of these media may be supplemented as necessary with serum, hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. In some preferred embodiments where selectable markers such as GS are utilized, for example, the media will lack glutamine. Any other necessary supplements may also be included at appropriate concentrations that would be known to those skilled in the art.

The present invention also contemplates the use of a variety of culture systems (e.g., petri dishes, 96 well plates, roller bottles, and bioreactors) for the transfected host cells. For example, the transfected host cells can be cultured in a perfusion system. Perfusion culture refers to providing a continuous flow of culture medium through a culture maintained at high cell density. The cells are suspended and do not require a solid support to grow on.

Generally, fresh nutrients must be supplied continuously with concomitant removal of toxic metabolites and, ideally, selective removal of dead cells. Filtering, entrapment and micro-capsulation methods are all suitable for refreshing the culture environment at sufficient rates.

As another example, in some embodiments a fed batch culture procedure can be employed. In the preferred fed batch culture the mammalian host, cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel). In some particularly preferred embodiments, the batch cultures are performed in roller bottles.

Further, the cells of the culture may be propagated according to any scheme or routine that may be suitable for the particular host cell and the particular production plan contemplated. Therefore, the present invention contemplates a single step or multiple step culture procedure. In a single step culture, the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

Fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen (dO2) and the like, are those used with the particular host and will be apparent to the ordinarily skilled artisan. Generally, the pH is adjusted to a level between about 6.5 and 7.5 using either an acid (e.g., CO2) or a base (e.g., Na2CO3 or NaOH). A suitable temperature range for culturing mammalian cells such as CHO cells is between about 30° to 38° C. and a suitable dO2 is between 5-90% of air saturation.

Following the polypeptide production phase, the polypeptide of interest is recovered from the culture medium using techniques that are well established in the art. The protein of interest preferably is recovered from the culture medium as a secreted polypeptide (e.g., the secretion of the protein of interest is directed by a signal peptide sequence), although it also may be recovered from host cell lysates. As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. Additionally, the protein of interest can be fused in frame to a marker sequence that allows for purification of the protein of interest. Non-limiting examples of marker sequences include a hexahistidine tag, which may be supplied by a vector, preferably a pQE-9 vector, and a hemagglutinin (HA) tag. The HA tag corresponds to an epitope derived from the influenza hemagglutinin protein (See e.g., Wilson et al., Cell, 37:767 [1984]). One skilled in the art will appreciate that purification methods suitable for the polypeptide of interest may require modification to account for changes in the character of the polypeptide upon expression in recombinant cell culture.

EXPERIMENTAL

The instant invention provides a unique way of combining retroviral transduction (referred to herein as GPEx® technology) in combination with a Glutamine Synthase (GS) knock-out CHO cell line system that has yielded unexpected improvement in the ability of the cells to produce high titers and specific productivities of the protein of interest. The GS knock-out cell line that was used in these studies was the CHOZN cell line available from MilliporeSigma. The GPEx® technology was practiced in a similar manner to what has been done previously in normal CHO cells. However, in the viral expression vector, the GS gene that is used for selection in GS knock-out cell line, was driven off the very weak promoter from the SIN (self-inactivating) LTR present in one of the versions of the GPEx expression vector that we use at Catalent. The combination of that vector, the normal GPEx cell line production process and the GS knock-out CHO cell line gave production levels of up to 7-fold greater than the traditional GPEx process in an unmodified CHO cell line.

Experiment 1:

Two pooled cell lines were produced from two different viral vectors. Both lines were produced using normal GPEx transduction processes and the GS knock-out cell line CHOZN. Both expression vectors were designed to express a test protein "Anyway".

Anyway is an Fc fusion protein. The only difference between the two expression vectors was that one vector after insertion into the cell line would have the full length Moloney Murine Leukemia Virus (MMLV) LTR driving expression of the GS gene and the other vector would have the MMLV SIN LTR driving expression of GS. The gene constructs used to produce the retrovector particles are provided in FIGS. 1 and 2. The sequences for the gene constructs are provided in FIGS. 3 and 4.

CHOZN Cell Line Development

Retrovector Production: The expression constructs outlined above were introduced into a HEK 293 cell line that constitutively produces the MLV gag, pro, and pol proteins. An envelope containing expression plasmid was also co-transfected with each of the gene constructs. The co-transfection resulted in the production of replication incompetent high titer retrovector that was concentrated by ultracentrifugation and used for cell transductions (1,2). Transduction using retrovectors produced using the above constructs into CHO cells results in the 3' LTR sequence being duplicated to the 5' end of the sequence replacing the hCMV-MoMuSV 5'LTR and subsequently controlling the expression of the GS gene in the pooled cell line.

Transduction of CHOZN Cells with Retrovector: Pooled cell lines containing retrovector insertions from each of the above constructs were made by performing transduction of the CHOZN Chinese Hamster Ovary parental cell line with retrovector made from the gene constructs developed to express the Anyway protein. A single cycle of transduction was performed to generate a pooled cell line for each of the two constructs. Upon completion of the cell transductions, the cell lines were placed in glutamine free medium to perform GS selection.

Fed Batch Production Anyway from the Two Pooled Population of Cells: Post-transduction, the pooled cell lines were scaled up for productivity in a fed batch study in duplicate 250 mL shake flasks. Each shake flask was seeded with 300,000 viable cells per mL in a 50 mL working volume of ExCell Advanced Fed Batch Medium (SAFC) and incubated in a humidified (70-80%) shaking incubator at 110 rpm with 5% CO2 and temperature of 37° C. Cultures were fed every other day starting on day 3 during the production using one feed supplement. Glucose was monitored daily and supplemented if the level dropped below 4 g/L. Cultures were terminated when viabilities were ≤50%.

Results

Figure 5:
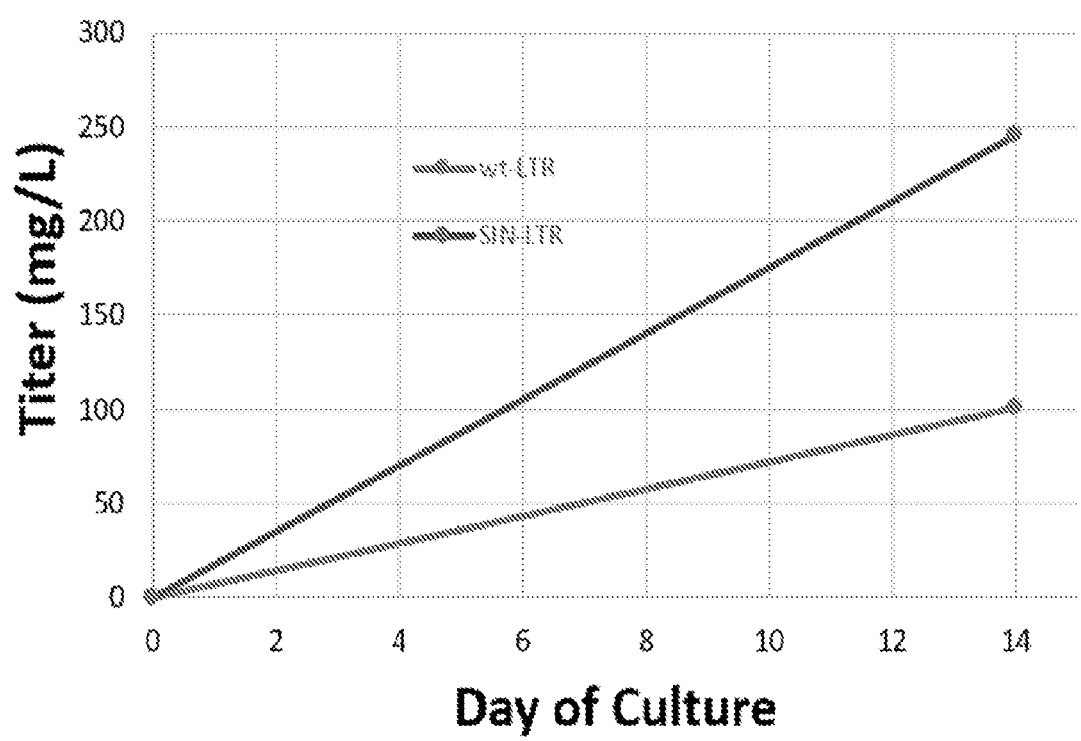
FIG. 5. Pooled cell line titer comparison between the full length MMLV construct and SIN MMLV LTR construct.

The results are presented in Table 1 and FIG. 5. These results are surprising. At similar average gene copy number for the two pools, there was major titer difference between the two pooled cell lines. So even at a slightly higher average gene copy number, the wild type or full length LTR gene construct gave significantly lower titers and this translated into significantly lower cell specific productivity per gene insert. A selection or competitive advantage for high expressing cells containing the SIN version of the gene construct is occurring.

TABLE 1

Pooled cell line comparison between the two gene constructs.

| Pooled Cell Lines | Average Pool Gene Copy Number | Final Titer (mg/L) | PCD/Gene Copy |
|---|---|---|---|
| wt-LTR | 19 | 101 | 0.0385 |
| SIN-LTR | 16 | 246 | 0.113 |

Experiment 2:

Based on the previous results we designed an experiment to compare the way we were traditionally practicing the GPEx technology to practicing the technology in exactly the same way but using the SIN-GS vector described above in combination with the CHOZN GS knock-out cell line. The processes were kept as similar as possible, with only two main differences. The first being that traditional GPEx uses the GPEx® Chinese Hamster Ovary (GCHO) parental cell line and the new version uses the CHOZN cell line. The second difference is the gene constructs used to make the retrovector were different. For traditional GPEx the construct does not contain the GS gene and for the new version it does contain the GS gene. All other components of the gene construct were similar. Each of the constructs again expresses the Anyway protein. After the pooled cell lines for each of the methods were completed, they were compared for production in a fed-batch culture analysis.

GCHO and CHOZN Cell Line Development:

Retrovector Production: The expression constructs were introduced into a HEK 293 cell line that constitutively produces the MLV gag, pro, and pol proteins. An envelope containing expression plasmid was also co-transfected with the each of the gene constructs. The co-transfection resulted in the production of replication incompetent high titer retrovector that was concentrated by ultracentrifugation and used for cell transductions (1,2).

Transduction of CHOZN Cells with Retrovector: Pooled cell lines containing retrovector insertions from each of the constructs were made by performing transduction of either the CHOZN Chinese Hamster Ovary parental cell line or the GCHO Chinese Hamster Ovary parental cell line with retrovector made from the either the gene construct containing GS or the gene construct without GS, both developed to express the Anyway protein. Three cycles of transduction were performed to generate a pooled cell line for each of the two constructs in the corresponding cell line. Additional cycles typically increase the number of inserts in the cell line and subsequently the gene copy number. Upon completion of each cycle of transduction the CHOZN based cell pools were placed in glutamine free medium for GS selection. The traditional GPEx cells underwent no selection as is the normal procedure.

Results

As expected the copy numbers increased for both methods with repeated cycles of transduction. However, significantly higher gene copy numbers were observed in each of the new GPEx cell pools compared to traditional GPEx as shown in Table 2.

TABLE 2

Pooled cell line gene copy numbers compared between the two different processes

| Transduction Cycle Number | Pooled Cell Line Copy Number | |
|---|---|---|
| | Traditional GPEx | New GPEx |
| 1x | 15 | 47 |
| 2x | 38 | 69 |
| 3x | 50 | 79 |

Fed Batch Production Anyway from the Two Pooled Population of Cells (3 Cycles of Transduction): Post-transduction, the pooled cell lines were scaled up for productivity in a fed batch study in duplicate 250 mL shake flasks. Each shake flask was seeded with 300,000 viable cells per mL in a 50 mL working volume of ActiPro media (HyClone) and incubated in a humidified (70-80%) shaking incubator at 120 rpm with 5% CO2 and temperature of 37° C. (34° C. starting day 6). Cultures were fed six times during the production run using two different feed supplements. Glucose was monitored daily and supplemented if the level dropped below 4 g/L. Cultures were terminated when viabilities were ≤50%.

Figure 6:
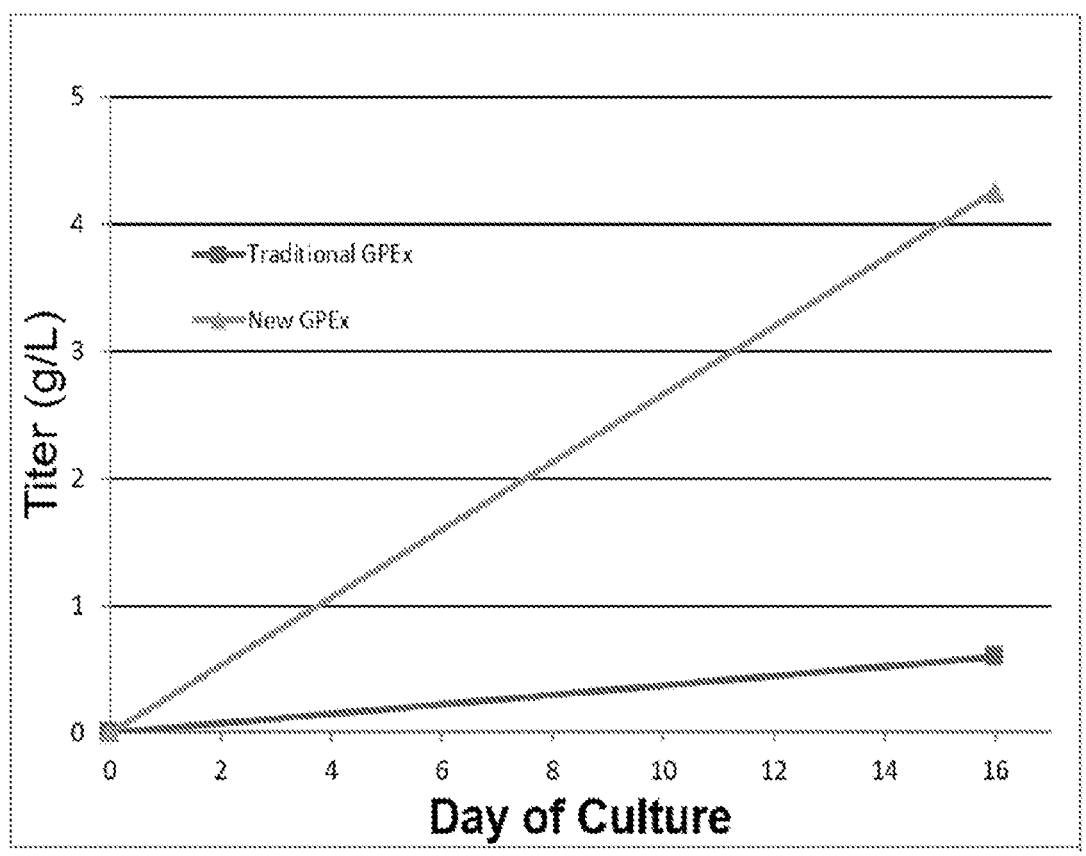
FIG. 6. Pooled cell line titer comparison between processes using the full length MMLV construct and SIN MMLV LTR construct.

The results are provided in Table 3 and FIG. 6. Again, a very unexpected result was observed. Optimized traditional GPEx clonal cell lines producing the Anyway product expressed at a maximum of 1.8 g/L and the new GPEx pool is over double that expression before any clonal selection. The new GPEx pool has both a higher copy number as well as more production per gene insert like was seen in experiment #1. The two of these together resulted in a significant difference in cellular specific productivity with close to a 3-fold higher pg/cell/day for the new GPEx pool. Overall viable cell density was also higher for the new GPEx pool compared to the traditional pool also aiding the substantial titer difference that was observed.

TABLE 3

Pooled cell line comparison between the two different processes for Anyway

| Pooled Cell Lines | Average Pool Gene Copy Number | Final Titer (g/L) | Specific Productivity pg/cell/day (PCD) | PCD/Gene Copy |
|---|---|---|---|---|
| Traditional GPEx 3x | 50 | 0.59 | 6.6 | 0.13 |
| New GPEx 3x | 79 | 4.25 | 15.2 | 0.19 |

Experiments 3 and 4:

The above data is for a Fc-Fusion produced from a single gene. Experiments 3 and 4 utilize transduction with separate heavy and light chain vectors (2 light chain transductions and 3 heavy chain transductions for both) with two different antibodies "Peelaway" and "Yourway" using both GPEx® technology and the new process using the SIN LTR to drive GS expression.

Retrovector Production: The expression constructs were introduced into a HEK 293 cell line that constitutively produces the MLV gag, pro, and pol proteins. An envelope containing expression plasmid was also co-transfected with the each of the gene constructs. The co-transfection resulted in the production of replication incompetent high titer retrovector that was concentrated by ultracentrifugation and used for cell transductions (1,2).

Transduction of CHOZN Cells with Retrovector: Pooled cell lines containing retrovector insertions from each of the constructs were made by performing transduction of either the CHOZN Chinese Hamster Ovary parental cell line or the GCHO Chinese Hamster Ovary parental cell line with retrovector made from the either the heavy and light chain gene constructs containing GS or the gene constructs without GS, developed to express the two different antibodies. Two cycles of light chain transduction and three cycles of heavy chain transduction were performed to generate a pooled cell line for each of the four constructs in each of the corresponding antibody cell lines. Additional cycles typically increase the number of inserts in the cell line and subsequently the gene copy number. Upon completion of each cycle of transduction the CHOZN based cell pools were placed in glutamine free medium for GS selection. The traditional GPEx cells underwent no selection as is the normal procedure.

Fed Batch Production Peelaway and Yourway from the Pooled Population Cell Lines (2 Light Chain Cycles of Transduction and 3 Heavy Chain Cycles of Transduction): Post-transduction, the pooled cell lines were scaled up for productivity in a fed batch study in duplicate 250 mL shake flasks. Each shake flask was seeded with 300,000 viable cells per mL in a 50 mL working volume of ActiPro media (HyClone) and incubated in a humidified (70-80%) shaking incubator at 120 rpm with 5% CO2 and temperature of 37° C. (34° C. starting day 6). Cultures were fed six times during the production run using two different feed supplements. Glucose was monitored daily and supplemented if the level dropped below 4 g/L. Cultures were terminated when viabilities were ≤50%.

Results

The results are presented in Tables 4 and 5. Significant advantages were observed for titer with the new vector and process.

TABLE 4

Pooled cell line comparison for Peelaway antibody between the two different processes

| Pooled Cell Lines | Final Titer (g/L) | Specific Productivity pg/cell/day (PCD) |
|---|---|---|
| Traditional GPEx 5x | 0.57 | 5.4 |
| New GPEx 5x | 1.79 | 9.6 |

TABLE 5

Pooled cell line comparison for Yourway
antibody between the two different processes

| Pooled Cell Lines | Final Titer (g/L) | Specific Productivity pg/cell/day (PCD) |
|---|---|---|
| Traditional GPEx 5x | 2.09 | 18.5 |
| New GPEx 5x | 3.66 | 14.0 |

Additional copy number analysis was performed on 4 Yourway cell pools. Cell pools generated after 1 light chain transduction and 2 heavy chain transduction cycles were compared to cell pools generated after 2 light chain transduction cycles and 3 heavy chain transduction cycles. Each of these two pooled cell lines were either set up to continue to grow in glutamine containing media or were place in media lacking glutamine. The gene copy number for the total number of genes, the number heavy chain genes and the number of light chain genes were calculated for each of the four pooled cell lines.

TABLE 6

| Pooled Cell Line | Glutamine +/− | Total Gene Copy # | Heavy Chain Gene Copy # | Light Chain Gene Copy # |
|---|---|---|---|---|
| LC1x/HC2x | + | 31 | 15 | 18 |
| LC1x/HC2x | − | 63 | 17 | 48 |
| LC2x/HC3x | + | 64 | 28 | 43 |
| LC2x/HC3x | − | 94 | 32 | 65 |

These data indicate that even though each of the cells in these pools have numerous copies of the GS gene being driven off the SIN LTR, there is significant selection occurring for those with more copies and, based on data above, those copies that are expressing at higher levels.

Experiment 5

For this experiment, the Yourway antibody product was used. The heavy chain gene construct used to generate the cell line was the same used in Experiment 4. The light chain gene construct was identical to the heavy chain gene construct in all aspects except that it contained the light chain coding sequence and it lacked the GS gene. A single transduction was performed for each the light chain (−GS) and heavy chain (+GS) containing retrovectors to generate a pooled cell line.

Retrovector Production: The expression constructs were introduced into a HEK 293 cell line that constitutively produces the MLV gag, pro, and pol proteins. An envelope containing expression plasmid was also co-transfected with the each of the gene constructs. The co-transfection resulted in the production of replication incompetent high titer retrovector that was concentrated by ultracentrifugation and used for cell transductions (1,2). Transduction of CHOZN Cells with Retrovector: Pooled cell lines containing retrovector insertions from each of the constructs were made by performing transduction of the CHOZN Chinese Hamster Ovary parental cell line with retrovector made from light chain gene constructs without GS and heavy chain constructs containing GS. One cycle of light chain transduction and one cycle of heavy chain transduction were performed to generate a pooled cell line. Upon completion of both cycles of transduction, the CHOZN based cell pool was split, with half being placed in glutamine free media and the other half continuing to be supplemented with glutamine during cell expansion and subsequent productivity assessment.

Fed Batch Production of Yourway from the Pooled Population Cell Lines (1 Light Chain Transduction and 1 Heavy Chain Transduction): The pooled cell lines were scaled up for productivity in a fed batch study in a 250 mL shake flask. The shake flasks were seeded with 300,000 viable cells per mL in a 50 mL working volume of ActiPro media (Hy Clone) and incubated in a humidified (70-80%) shaking incubator at 120 rpm with 5% $CO_2$ and temperature of 37° C. (34° C. starting day 6). Cultures were fed six times during the production run using two different feed supplements. Glucose was monitored daily and supplemented if the level dropped below 4 g/L. Glutamine supplemented cultures were monitored daily for glutamine and fed if the level dropped below 2 mM. Cultures were terminated when viabilities were ≤50%.

Results

The results are presented in Table 7. Selection by removing glutamine significantly increased the heavy chain gene copy number of the cell pool. Somewhat surprisingly the light chain copy number also increased, but not to the same extent as the heavy chain. Total antibody production was also significantly higher than the culture that was unselected with levels reaching those shown in Table 5 with only two transductions performed instead of the five that were completed for that experiment.

TABLE 7

Pooled cell line comparison for Yourway antibody with and
without glutamine selection. The pooled cell line was produced
from a single light chain transduction (−GS) and
a single heavy chain transduction (+GS).

| Pooled Cell Lines | Average Pool Heavy Chain Copy Number | Average Pool Light Chain Copy Number | Final Titer (mg/L) |
|---|---|---|---|
| + Glutamine | 2.1 | 12.5 | 516 |
| − Glutamine | 24.1 | 36.0 | 3,323 |

Experiment 6

Figure 8:
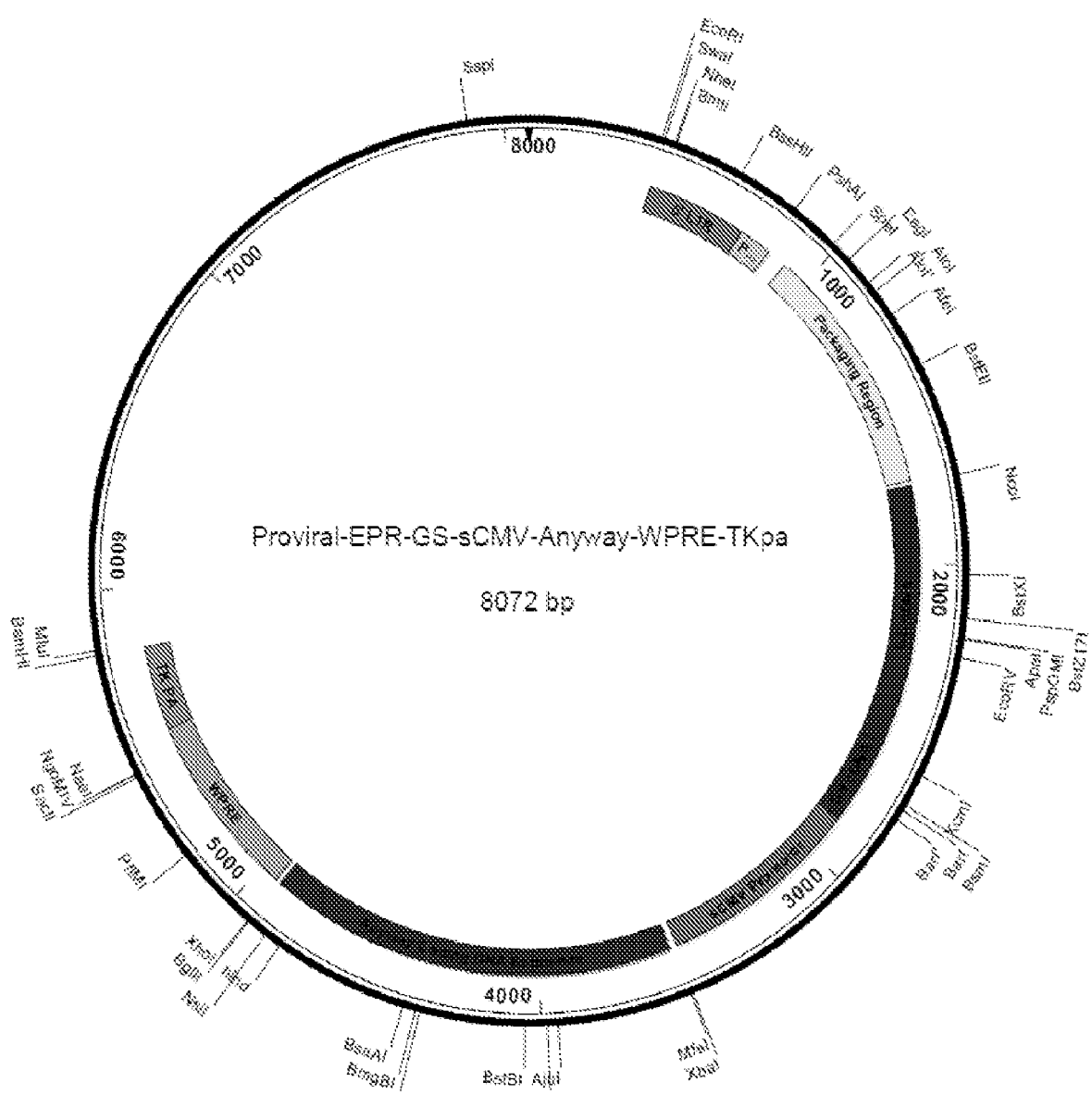
FIG. 8. Map of proviral plasmid construct (SEQ ID NO: 4).

A gene construct was designed and produced to test if the technology would behave similarly using traditional cell transfection methodologies as compared to retrovector transduction. One example of a traditional plasmid transfection construct that was generated is shown in FIG. 8 (Plasmid map) and FIG. 9 (Actual plasmid sequence; SEQ ID NO:4).

1. Bleck, G. T. 2005 An alternative method for the rapid generation of stable, high-expressing mammalian cell lines (A Technical Review). Bioprocessing J. September/October pp 1-7.
2. Bleck. G. T., 2010. GPEx® A Flexible Method for the Rapid Generation of Stable, High Expressing, Antibody Producing Mammalian Cell Lines Chapter 4 In: Current Trends in Monoclonal Antibody Development and Manufacturing, Biotechnology: Pharmaceutical Aspects, Edited by: S. J. Shire et al. @ 2010 American Association of Pharmaceutical Scientists, DOI 10.1007/978-0-387-76643-0_4.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

What is claimed is:

1. A vector for expression of a protein of interest comprising a nucleic acid sequence encoding a selectable marker in operable association with a first promoter sequence and a nucleic acid sequence encoding the protein of interest operably linked to a second promoter sequence, wherein the first promoter sequence is a viral Self-Inactivating (SIN) Long Terminal Repeat (LTR) promoter sequence that is at least 95% identical to SEQ ID NO:3.

2. The vector of claim 1, wherein the SIN LTR promoter sequence is SEQ ID NO:3.

3. The vector of claim 1, wherein the selectable marker is Glutamine Synthetase (GS).

4. The vector of claim 1, wherein the selectable marker is Dihydrofolate Reductase (DHFR).

5. The vector of claim 1, wherein the vector comprises a single poly A signal sequence in operable association with said selectable marker and said nucleic acid encoding the protein of interest.

6. The vector of claim 1, wherein the vector comprises a first poly A signal sequence in operable association with said selectable marker and a second poly A signal sequence in operable association with said nucleic acid encoding the protein of interest.

7. The vector of claim 1, wherein the protein of interest is selected from the group consisting of an Fc-fusion protein, an enzyme, an albumin fusion, a growth factor, a protein receptor, a single chain antibody (scFv), a single chain-Fc (scFv-Fc), a diabody, and minibody (scFv-CH3), Fab, single chain Fab (scFab), an immunoglobulin heavy chain, and an immunoglobulin light chain.

8. The vector of claim 1, wherein the vector is a retroviral vector.

9. The vector of claim 1, wherein said vector is a plasmid.

10. A host cell comprising the vector of claim 1.

11. The host cell of claim 10, wherein the host cell is a GS knockout cell line.

12. The host cell of claim 11, wherein the host cell is a DHFR knockout cell.

13. The host cell of claim 10, wherein the host cell is selected from the group consisting of a Chinese Hamster Ovary (CHO) cell, a HEK 293 cell and a CAP cell.

14. The host cell of claim 10, wherein the host cell comprises from about 1 to 1000 copies of the vector.

15. The host cell of claim 10, wherein the host cell further comprises at least a second vector that encodes and allows for expression of a second protein of interest, and wherein said second vector does not include a selectable marker.

16. The host cell of claim 15, wherein the first protein of interest in the first vector is one of an immunoglobulin heavy or light chain and the second protein in the second vector is the other of an immunoglobulin heavy or light chain.

17. A host cell culture comprising host cells according to claim 10.

18. A process for producing a protein of interest comprising culturing host cells according to claim 10 and purifying the protein of interest from the host cell culture.

* * * * *

SEQUENCE LISTING

<160> NUMBER OF SEQ ID NOS: 4

<210> SEQ ID NO 1
<211> LENGTH: 6217
<212> TYPE: DNA
<213> ORGANISM: Artificial sequence
<220> FEATURE:
<223> OTHER INFORMATION: Synthetic construct

<400> SEQUENCE: 1

| | | | | | |
|---|---|---|---|---|---|
| gtccggccat | tagccatatt | attcattggt | tatatagcat | aaatcaatat | tggctattgg | 60 |
| ccattgcata | cgttgtatcc | atatcataat | atgtacattt | atattggctc | atgtccaaca | 120 |
| ttaccgccat | gttgacattg | attattgact | agttattaat | agtaatcaat | tacggggtca | 180 |
| ttagttcata | gcccatatat | ggagttccgc | gttacataac | ttacggtaaa | tggcccgcct | 240 |
| ggctgaccgc | ccaacgaccc | ccgcccattg | acgtcaataa | tgacgtatgt | tcccatagta | 300 |
| acgccaatag | ggactttcca | ttgacgtcaa | tgggtggagt | atttacgtaa | aactgcccac | 360 |
| ttggcagtac | atcaagtgta | tcatatgcca | agtacgcccc | ctattgacgt | caatgacggt | 420 |
| aaatggcccg | cctggcatta | tgcccagtac | atgaccttat | gggactttcc | tacttggcag | 480 |
| tacatctacg | tattagtcat | cgctattacc | atggtgatgc | ggttttggca | gtacatcaat | 540 |
| gggcgtggat | agcggtttga | ctcacgggga | tttccaagtc | tccacccat | tgacgtcaat | 600 |
| gggagtttgt | tttggcacca | aaatcaacgg | gactttccaa | aatgtcgtaa | caactccgcc | 660 |
| ccattgacgc | aaatgggcgg | taggcgtgta | cggtgggagg | tctatataag | cagagctcaa | 720 |
| taaaagagcc | cacaacccct | cactcggcgc | gccagtcttc | cgatagactg | cgtcgcccgg | 780 |
| gtacccgtat | tcccaataaa | gcctcttgct | gtttgcatcc | gaatcgtggt | ctcgctgttc | 840 |
| cttgggaggg | tctcctctga | gtgattgact | acccacgacg | ggggtctttc | atttggggc | 900 |
| tcgtccggga | tttggagacc | cctgcccagg | gaccaccgac | ccaccaccgg | gaggtaagct | 960 |
| ggccagcaac | ttatctgtgt | ctgtccgatt | gtctagtgtc | tatgtttgat | gttatgcgcc | 1020 |
| tgcgtctgta | ctagttagct | aactagctct | gtatctggcg | gacccgtggt | ggaactgacg | 1080 |
| agttctgaac | acccggccgc | aaccctggga | gacgtcccag | ggactttggg | ggccgttttt | 1140 |
| gtggcccgac | ctgaggaagg | gagtcgatgt | ggaatccgac | cccgtcagga | tatgtggttc | 1200 |
| tggtaggaga | cgagaaccta | aaacagttcc | cgcctccgtc | tgaattttg | ctttcggttt | 1260 |
| ggaaccgaag | ccgcgcgtct | tgtctgctgc | agcgctgcag | catcgttctg | tgttgtctct | 1320 |
| gtctgactgt | gtttctgtat | ttgtctgaaa | attagggcca | gactgttacc | actcccttaa | 1380 |
| gtttgacctt | aggtcactgg | aaagatgtcg | agcggatcgc | tcacaaccag | tcggtagatg | 1440 |
| tcaagaagag | acgttgggtt | accttctgct | ctgcagaatg | gccaaccttt | aacgtcggat | 1500 |
| ggccgcgaga | cggcacctttt | aaccgagacc | tcatcaccca | ggttaagatc | aaggtctttt | 1560 |
| cacctggccc | gcatggacac | ccagaccagg | tcccctacat | cgtgacctgg | gaagccttgg | 1620 |
| cttttgaccc | ccctccctgg | gtcaagccct | ttgtacaccc | taagcctccg | cctcctcttc | 1680 |
| ctccatccgc | cccgtctctc | ccccttgaac | ctcctcgttc | gaccccgcct | cgatcctccc | 1740 |
| tttatccagc | cctcactcct | tctctaggcg | ccggaattgc | cttccaccat | ggccacctca | 1800 |
| gcaagttccc | acttgaacaa | aaacatcaag | caaatgtact | tgtgcctgcc | caggtgag | 1860 |
| aaagtccaag | ccatgtatat | ctgggttgat | ggtactggag | aaggactgcg | ctgcaaaacc | 1920 |
| cgcaccctgg | actgtgagcc | caagtgtgta | aagagttac | ctgagtggaa | ttttgatggc | 1980 |
| tctagtacct | ttcagtctga | gggctccaac | agtgacatgt | atctcagccc | tgttgccatg | 2040 |

```
tttcgggacc ccttccgcag agatcccaac aagctggtgt tctgtgaagt tttcaagtac    2100
aaccggaagc ctgcagagac caatttaagg cactcgtgta aacggataat ggacatggtg    2160
agcaaccagc acccctggtt tggaatggaa caggagtata ctctgatggg aacagatggg    2220 caccctttg gttggccttc caatggcttt cctgggcccc aaggtccgta ttactgtggt     2280
gtgggcgcag acaaagccta tggcagggat atcgtggagg ctcactaccg cgcctgcttg    2340
tatgctgggg tcaagattac aggaacaaat gctgaggtca tgcctgccca gtgggagttc    2400
caaataggac cctgtgaagg aatccgcatg ggagatcatc tctgggtggc ccgtttcatc    2460
ttgcatcgga tatgtgaaga ctttggggta atagcaacct tgaccccaa gcccattcct     2520 gggaactgga atggtgcagg ctgccatacc aactttagca ccaaggccat gcgggaggag    2580
aatggtctga gcacatcga ggaggccatc gagaaactaa gcaagcggca ccggtaccac     2640
attcgagcct acgatcccaa gggggcctg acaatgccc gtcgtctgac tgggttccac      2700
gaaacgtcca acatcaacga cttttctgct ggtgtcgcca atcgcagtgc cagcatccgc    2760
attccccgga ctgtcggcca ggagaagaaa ggttactttg aagaccgccg cccctctgcc    2820
aactgtgacc cctttgcagt gacagaagcc atcgtccgca catgccttct caatgagact    2880
ggcgacgagc ccttccaata caaaaactaa agatccctat ggctattggc caggttcaat    2940
actatgtatt ggccctatgc catatagtat tccatatatg ggttttccta ttgacgtaga    3000
tagcccctcc caatgggcgg tcccatatac catatatggg gcttcctaat accgccata    3060 gccactcccc cattgacgtc aatggtctct atatatggtc tttcctattg acgtcatatg    3120
ggcggtccta ttgacgtata tggcgcctcc cccattgacg tcaattacgg taaatggccc    3180
gcctggctca atgcccattg acgtcaatag gaccacccac cattgacgtc aatgggatgg    3240
ctcattgccc attcatatcc gttctcacgc cccctattga cgtcaatgac ggtaaatggc    3300
ccacttggca gtacatcaat atctattaat agtaacttgg caagtacatt actattggaa    3360
gtacgccagg gtacattggc agtactccca ttgacgtcaa tggcggtaaa tggcccgcga    3420
tggctgccaa gtacatcccc attgacgtca atggggaggg gcaatgacgc aaatgggcgt    3480
tccattgacg taaatgggcg gtaggcgtgc ctaatgggag gtctatataa gcaatgctcg    3540
tttagggaac cgccattctg cctggggacg tcggaggagc tcgaaagctt ctagacaatt    3600
gccgccacca tgatgtcctt tgtctctctg ctcctggttg gcatcctatt ccatgccacc    3660
caggccagtg atacaggtag acctttcgta gagatgtaca gtgaaatccc cgaaattata    3720
cacatgactg aaggaaggga gctcgtcatt ccctgccggg ttacgtcacc taacatcact    3780
gttactttaa aaagtttcc acttgacact tgatccctg atggaaaacg cataatctgg     3840
gacagtagaa agggcttcat catatcaaat gcaacgtaca agaaatagg gcttctgacc    3900 tgtgaagcaa cagtcaatgg gcatttgtat aagacaaact atctcacaca tcgacaaacc    3960
aatacaatca tagatgtcgt tctgagtccg tctcatggaa ttgaactatc tgttggagaa    4020
aagcttgtct taaattgtac agcaagaact gaactaaatg tggggattga cttcaactgg    4080 gaatacccctt cttcgaagca tcagcataag aaacttgtaa accgagacct aaaaacccag    4140
tctgggagtg agatgaagaa gttttttgagc accttaacta tagatggtgt aacccggagt    4200
gaccaaggat tgtacacctg tgcagcatcc agtgggctga tgaccaagaa aaacagcaca    4260
tttgtcaggg tccatgaaaa agacaaaaact cacacatgcc caccgtgccc agcacctgaa    4320
ctcctggggg gaccctcagt cttcctcttc cccccaaaac ccaaggacac cctcatgatc    4380
```

-continued

| | |
|---|---|
| tcccggaccc ctgaggtcac atgcgtggtg gtggacgtga gccacgaaga ccctgaggtc | 4440 |
| aagttcaact ggtacgtgga cggcgtggag gtgcataatg ccaagacaaa gccacgggag | 4500 |
| gagcagtaca acagcacata tcgtgtggtc agcgtcctca ccgtcctgca ccaggactgg | 4560 |
| ctgaatggca aggagtacaa gtgcaaggtc tccaacaaag ccctcccagc ccccatcgag | 4620 |
| aaaaccatct ccaaagccaa agggcagccc cgagaaccac aggtgtacac cctgccccca | 4680 |
| tcccgggatg agctgaccaa gaaccaggtc agcctgacct gcctggtcaa aggcttctat | 4740 |
| cccagcgaca tcgccgtgga gtgggagagc aatgggcagc cggagaacaa ctacaagacc | 4800 |
| acgcctcccg tgctggactc cgacggctcc ttcttcctct acagcaagct caccgtggac | 4860 |
| aagagcaggt ggcagcaggg gaacgtcttc tcatgctccg tgatgcatga ggctctgcac | 4920 |
| aaccactaca cgcagaagag cctctccctg tctcccggga atgatgaga tctcgagttc | 4980 |
| gacatcgata atcaacctct ggattacaaa atttgtgaaa gattgactgg tattcttaac | 5040 |
| tatgttgctc cttttacgct atgtggatac gctgctttaa tgcctttgta tcatgctatt | 5100 |
| gcttcccgta tggctttcat tttctcctcc ttgtataaat cctggttgct gtctctttat | 5160 |
| gaggagttgt ggcccgttgt caggcaacgt ggcgtggtgt gcactgtgtt tgctgacgca | 5220 |
| acccccactg gttggggcat tgccaccacc tgtcagctcc tttccgggac tttcgctttc | 5280 |
| cccctcccta ttgccacggc ggaactcatc gccgcctgcc ttgcccgctg ctggacaggg | 5340 |
| gctcggctgt tgggcactga caattccgtg gtgttgtcgg ggaaatcatc gtcctttcct | 5400 |
| tggctgctcg cctgtgttgc cacctggatt ctgcgcggga cgtccttctg ctacgtccct | 5460 |
| tcggccctca atccagcgga ccttccttcc cgcggcctgc tgccggctct gcggcctctt | 5520 |
| ccgcgtcttc gccttcgccc tcagacgagt cggatctccc tttgggccgc ctccccgcat | 5580 |
| cgataaaata aaagatttta tttagtctcc agaaaagggg ggaatgaaa gaccccacct | 5640 |
| gtaggtttgg caagctagct taagtaacgc cattttgcaa ggcatggaaa atacataac | 5700 |
| tgagaataga gaagttcaga tcaaggtcag gaacagatgg aacagctgaa tatgggccaa | 5760 |
| acaggatatc tgtggtaagc agttcctgcc ccggctcagg gccaagaaca gatggaacag | 5820 |
| ctgaatatgg gccaaacagg atatctgtgg taagcagttc ctgccccggc tcagggccaa | 5880 |
| gaacagatgg tccccagatg cggtccagcc ctcagcagtt tctagagaac catcagatgt | 5940 |
| ttccagggtg ccccaaggac ctgaaatgac cctgtgcctt atttgaacta accaatcagt | 6000 |
| tcgcttctcg cttctgttcg cgcgcttctg ctccccgagc tcaataaaag agcccacaac | 6060 |
| ccctcactcg gggcgccagt cctccgatty actgagtcgc ccgggtaccc gtgtatccaa | 6120 |
| taaaccctct tgcagttgca tccgacttgt ggtctcgctg ttccttggga gggtctcctc | 6180 |
| tgagtgattg actacccgtc agcgggggtc tttcatt | 6217 |

<210> SEQ ID NO 2
<211> LENGTH: 6065
<212> TYPE: DNA
<213> ORGANISM: Artificial sequence
<220> FEATURE:
<223> OTHER INFORMATION: Synthetic construct

<400> SEQUENCE: 2

| | |
|---|---|
| gtccggccat tagccatatt attcattggt tatatagcat aaatcaatat tggctattgg | 60 |
| ccattgcata cgttgtatcc atatcataat atgtacattt atattggctc atgtccaaca | 120 |
| ttaccgccat gttgacattg attattgact agttattaat agtaatcaat tacgggtca | 180 |
| ttagttcata gcccatatat ggagttccgc gttacataac ttacggtaaa tggcccgcct | 240 |

| | |
|---|---|
| ggctgaccgc ccaacgaccc ccgcccattg acgtcaataa tgacgtatgt tcccatagta | 300 |
| acgccaatag ggactttcca ttgacgtcaa tgggtggagt atttacggta aactgcccac | 360 |
| ttggcagtac atcaagtgta tcatatgcca agtacgcccc ctattgacgt caatgacggt | 420 |
| aaatggcccg cctggcatta tgcccagtac atgaccttat gggactttcc tacttggcag | 480 |
| tacatctacg tattagtcat cgctattacc atggtgatgc ggttttggca gtacatcaat | 540 |
| gggcgtggat agcggtttga ctcacgggga tttccaagtc tccacccat tgacgtcaat | 600 |
| gggagtttgt tttggcacca aaatcaacgg gactttccaa atgtcgtaa caactccgcc | 660 |
| ccattgacgc aaatgggcgg taggcgtgta cggtgggagg tctatataag cagagctcaa | 720 |
| taaaagagcc cacaacccct cactcggcgc gccagtcttc cgatagactg cgtcgcccgg | 780 |
| gtacccgtat tcccaataaa gcctcttgct gtttgcatcc gaatcgtggt ctcgctgttc | 840 |
| cttgggaggg tctcctctga gtgattgact acccacgacg ggggtctttc atttgggggc | 900 |
| tcgtccggga tttggagacc cctgcccagg gaccaccgac ccaccaccgg gaggtaagct | 960 |
| ggccagcaac ttatctgtgt ctgtccgatt gtctagtgtc tatgtttgat gttatgcgcc | 1020 |
| tgcgtctgta ctagttagct aactagctct gtatctggcg gacccgtggt ggaactgacg | 1080 |
| agttctgaac accggccgc aaccctggga gacgtcccag ggactttggg ggccgttttt | 1140 |
| gtggcccgac ctgaggaagg gagtcgatgt ggaatccgac cccgtcagga tatgtggttc | 1200 |
| tggtaggaga cgagaaccta aaacagttcc cgcctccgtc tgaattttg ctttcggttt | 1260 |
| ggaaccgaag ccgcgcgtct tgtctgctgc agcgctgcag catcgttctg tgttgtctct | 1320 |
| gtctgactgt gtttctgtat ttgtctgaaa attagggcca gactgttacc actcccttaa | 1380 |
| gtttgacctt aggtcactgg aaagatgtcg agcggatcgc tcacaaccag tcggtagatg | 1440 |
| tcaagaagag acgttgggtt accttctgct ctgcagaatg gccaaccttt aacgtcggat | 1500 |
| ggccgcgaga cggcaccttt aaccgagacc tcatcccca ggttaagatc aaggtctttt | 1560 |
| cacctggccc gcatggacac ccagaccagg tccctacat cgtgacctgg gaagccttgg | 1620 |
| cttttgaccc ccctccctgg gtcaagccct ttgtacaccc taagcctccg cctcctcttc | 1680 |
| ctccatccgc cccgtctctc cccttgaac ctcctcgttc gaccccgcct cgatcctccc | 1740 |
| tttatccagc cctcactcct tctctaggcg ccggaattgc cttccaccat ggccacctca | 1800 |
| gcaagttccc acttgaacaa aaacatcaag caaatgtact tgtgcctgcc ccagggtgag | 1860 |
| aaagtccaag ccatgtatat ctgggttgat ggtactggag aaggactgcg ctgcaaaacc | 1920 |
| cgcaccctgg actgtgagcc caagtgtgta aagagttac ctgagtggaa ttttgatggc | 1980 |
| tctagtacct ttcagtctga gggctccaac agtgacatgt atctcagccc tgttgccatg | 2040 |
| tttcgggacc ccttccgcag agatcccaac aagctggtgt tctgtgaagt tttcaagtac | 2100 |
| aaccggaagc ctgcagagac caatttaagg cactcgtgta aacggataat ggacatggtg | 2160 |
| agcaaccagc acccctggtt tggaatgaa caggagtata tctctgatgg aacagatggg | 2220 |
| caccctttg gttggccttc caatggcttt cctgggcccc aaggtccgta ttactgtggt | 2280 |
| gtgggcgcag acaaagccta tggcaggat atcgtggagg ctcactaccg cgcctgcttg | 2340 |
| tatgctgggg tcaagattac aggaacaaat gctgaggtca tgcctgccca gtgggagttc | 2400 |
| caaataggac cctgtgaagg aatccgcatg ggagatcatc tctgggtggc ccgtttcatc | 2460 |
| ttgcatcgag tatgtgaaga ctttgggggta atagcaacct tgacccaa gcccattcct | 2520 |
| gggaactgga atggtgcagg ctgccatacc aactttagca ccaaggccat gcgggaggag | 2580 |

```
aatggtctga agcacatcga ggaggccatc gagaaactaa gcaagcggca ccggtaccac    2640
attcgagcct acgatcccaa gggggggcctg acaatgccc gtcgtctgac tgggttccac    2700
gaaacgtcca acatcaacga ctttctgct ggtgtcgcca atcgcagtgc cagcatccgc    2760
attccccgga ctgtcggcca ggagaagaaa ggttactttg aagaccgccg cccctctgcc    2820
aactgtgacc ccttttgcagt gacagaagcc atcgtccgca catgccttct caatgagact    2880
ggcgacgagc ccttccaata caaaaactaa agatccctat ggctattggc caggttcaat    2940
actatgtatt ggccctatgc catatagtat tccatatatg ggttttccta ttgacgtaga    3000
tagcccctcc caatgggcgg tcccatatac catatatggg gcttcctaat accgcccata    3060
gccactcccc cattgacgtc aatggtctct atatatggtc tttcctattg acgtcatatg    3120
ggcggtccta ttgacgtata tggcgcctcc cccattgacg tcaattacgg taaatggccc    3180
gcctggctca atgcccattg acgtcaatag gaccacccac cattgacgtc aatgggatgg    3240
ctcattgccc attcatatcc gttctcacgc cccctattga cgtcaatgac ggtaaatggc    3300
ccacttggca gtacatcaat atctattaat agtaacttgg caagtacatt actattggaa    3360
gtacgccagg gtacattggc agtactccca ttgacgtcaa tggcggtaaa tgggcccgcga    3420 tggctgccaa gtacatcccc attgacgtca atggggaggg gcaatgacgc aaatgggcgt    3480
tccattgacg taaatgggcg gtaggcgtgc ctaatgggag gtctatataa gcaatgctcg    3540
tttagggaac cgccattctg cctggggacg tcggaggagc tcgaaagctt ctagacaatt    3600
gccgccacca tgatgtcctt tgtctctctg ctcctggttg gcatcctatt ccatgccacc    3660
caggccagtg atacaggtag accttttcgta gagatgtaca gtgaaatccc cgaaattata    3720
cacatgactg aaggaaggga gctcgtcatt ccctgccggg ttacgtcacc taacatcact    3780
gttactttaa aaagtttcc acttgacact ttgatccctg atggaaaacg cataatctgg    3840
gacagtagaa agggcttcat catatcaaat gcaacgtaca agaaatagg gcttctgacc    3900 tgtgaagcaa cagtcaatgg gcatttgtat aagacaaact atctcacaca tcgacaaacc    3960
aatacaatca tagatgtcgt tctgagtccg tctcatggaa ttgaactatc tgttggagaa    4020
aagcttgtct taaattgtac agcaagaact gaactaaatg tggggattga cttcaactgg    4080 gaatacccctt cttcgaagca tcagcataag aaacttgtaa accgagacct aaaaacccag    4140
tctgggagtg agatgaagaa gttttttgagc accttaacta tagatggtgt aacccggagt    4200
gaccaaggat tgtacacctg tgcagcatcc agtgggctga tgaccaagaa aaacagcaca    4260
tttgtcaggg tccatgaaaa agacaaaact cacacatgcc caccgtgccc agcacctgaa    4320
ctcctggggg gaccctcagt cttcctcttc cccccaaaac ccaaggacac cctcatgatc    4380
tcccggaccc ctgaggtcac atgcgtggtg gtggacgtga gccacgaaga ccctgaggtc    4440
aagttcaact ggtacgtgga cggcgtggag gtgcataatg ccaagacaaa gccacgggag    4500
gagcagtaca acagcacata tcgtgtggtc agcgtcctca ccgtcctgca ccaggactgg    4560
ctgaatggca aggagtacaa gtgcaaggtc tccaacaaag ccctcccagc ccccatcgag    4620
aaaaccatct ccaaagccaa agggcagccc cgagaaccac aggtgtacac cctgccccca    4680
tcccgggatg agctgaccaa gaaccaggtc agcctgacct gcctggtcaa aggcttctat    4740
cccagcgaca tcgccgtgga gtgggagagc aatgggcagc cggagaacaa ctacaagacc    4800
acgcctcccg tgctggactc cgacggctcc ttcttcctct acagcaagct caccgtggac    4860
aagagcaggt ggcagcaggg gaacgtcttc tcatgctccg tgatgcatga ggctctgcac    4920
aaccactaca cgcagaagag cctctcccctg tctcccggga aatgatgaga tctcgagttc    4980
```

```
gacatcgata atcaacctct ggattacaaa atttgtgaaa gattgactgg tattcttaac    5040
tatgttgctc cttttacgct atgtggatac gctgctttaa tgcctttgta tcatgctatt    5100
gcttcccgta tggctttcat tttctcctcc ttgtataaat cctggttgct gtctctttat    5160
gaggagttgt ggcccgttgt caggcaacgt ggcgtggtgt gcactgtgtt tgctgacgca    5220 accccactg  gttggggcat tgccaccacc tgtcagctcc tttccgggac tttcgctttc    5280
cccctcccta ttgccacggc ggaactcatc gccgcctgcc ttgcccgctg ctggacaggg    5340
gctcggctgt tgggcactga caattccgtg gtgttgtcgg ggaaatcatc gtcctttcct    5400
tggctgctcg cctgtgttgc cacctggatt ctgcgcggga cgtccttctg ctacgtccct    5460
tcggccctca atccagcgga ccttccttcc cgcggcctgc tgccggctct gcggcctctt    5520
ccgcgtcttc gccttcgccc tcagacgagt cggatctccc tttgggccgc ctccccgcat    5580
cgataaaata aagattttta tttagtctcc agaaaaaggg gggaatgaaa gaccccacct    5640
gtaggtttgg caagctagct taagtaacgc cattttgcaa ggcatggaaa aatacataac    5700
tgagaataga gaagttcaga tcaaggtcag gaacagatgg aacagggtcg accggtcgac    5760
cggtcgaccc tagagaacca tcagatgttt ccagggtgcc ccaaggacct gaaatgaccc    5820
tgtgccttat ttgaactaac caatcagttc gcttctcgct tctgttcgcg cgcttctgct    5880
ccccgagctc aataaaagag cccacaaccc ctcactcggg gcgccagtcc tccgattgac    5940
tgagtcgccc gggtacccgt gtatccaata aaccctcttg cagttgcatc cgacttgtgg    6000
tctcgctgtt ccttgggagg gtctcctctg agtgattgac tacccgtcag cgggggtctt    6060
tcatt                                                                6065

<210> SEQ ID NO 3
<211> LENGTH: 442
<212> TYPE: DNA
<213> ORGANISM: Artificial sequence
<220> FEATURE:
<223> OTHER INFORMATION: Synthetic construct

<400> SEQUENCE: 3
aatgaaagac cccacctgta ggtttggcaa gctagcttaa gtaacgccat tttgcaaggc      60
atggaaaaat acataactga gaatagagaa gttcagatca aggtcaggaa cagatggaac    120
agggtcgacc ggtcgaccgg tcgaccctag agaaccatca gatgtttcca gggtgcccca    180
aggacctgaa atgaccctgt gccttatttg aactaaccaa tcagttcgct tctcgcttct    240
gttcgcgcgc ttctgctccc cgagctcaat aaaagagccc acaacccctc actcggggcg    300
ccagtcctcc gattgactga gtcgcccggg tacccgtgta tccaataaac cctcttgcag    360
ttgcatccga cttgtggtct cgctgttcct tgggagggtc cctctgagt gattgactac    420 ccgtcagcgg ggtctttca tt                                              442

<210> SEQ ID NO 4
<211> LENGTH: 8072
<212> TYPE: DNA
<213> ORGANISM: Artificial sequence
<220> FEATURE:
<223> OTHER INFORMATION: Synthetic construct

<400> SEQUENCE: 4
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
```

-continued

```
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt catttaaatg aaagacccca    420
cctgtaggtt tggcaagcta gcttaagtaa cgccattttg caaggcatgg aaaaatacat    480
aactgagaat agaaaagttc agatcaaggt caggaacaga tggaacaggg tcgaccggtc    540
gaccggtcga ccctagagaa ccatcagatg tttccagggt gccccaagga cctgaaatga    600
ccctgtgcct tatttgaact aaccaatcag ttcgcttctc gcttctgttc gcgcgcttct    660
gctccccgag ctcaataaaa gagcccacaa cccctcactc ggggcgccag tcttccgata    720
gactgcgtcg cccgggtacc cgtattccca ataaagcctc ttgctgtttg catccgaatc    780
gtggtctcgc tgttccttgg gagggtctcc tctgagtgat tgactaccca cgacggggt    840 cttcatttg ggggctcgtc cgggatttgg agacccctgc ccaggacca ccgacccacc    900 accgggaggt aagctggcca gcaacttatc tgtgtctgtc cgattgtcta gtgtctatgt    960
ttgatgttat gcgcctgcgt ctgtactagt tagctaacta gctctgtatc tggcggaccc    1020
gtggtggaac tgacgagttc tgaacacccg ccgcaaccc tgggagacgt cccagggact    1080
ttgggggccg ttttgtggc ccgacctgag gaagggagtc gatgtggaat ccgaccccgt    1140
caggatatgt ggttctggta ggagacgaga acctaaaaca gttcccgcct ccgtctgaat    1200
ttttgctttc ggtttggaac cgaagccgcg cgtcttgtct gctgcagcgc tgcagcatcg    1260
ttctgtgttg tctctgtctg actgtgtttc tgtatttgtc tgaaaattag gccagactg    1320 ttaccactcc cttaagtttg accttaggtc actggaaaga tgtcgagcgg atcgctcaca    1380
accagtcggt agatgtcaag aagagacgtt gggttacctt ctgctctgca gaatggccaa    1440
cctttaacgt cggatggccg cgagacggca ccttttaaccg agacctcatc acccaggtta    1500
agatcaaggt cttttcacct ggcccgcatg gacacccaga ccaggtcccc tacatcgtga    1560
cctgggaagc cttggctttt gaccccctc cctgggtcaa gccctttgta caccctaagc    1620
ctccgcctcc tcttcctcca tccgccccgt ctctccccct tgaacctcct cgttcgaccc    1680
cgcctcgatc ctcccttat ccagcccca ctccttctct aggcgccgga attgccttcc    1740
accatggcca cctcagcaag ttcccacttg aacaaaaaca tcaagcaaat gtacttgtgc    1800
ctgccccagg gtgagaaagt ccaagccatg tatatctggg ttgatggtac tggagaagga    1860
ctgcgctgca aaacccgcac cctggactgt gagcccaagt gtgtagaaga gttacctgag    1920
tggaattttg atggctctag tacctttcag tctgagggct ccaacagtga catgtatctc    1980
agccctgttg ccatgtttcg ggacccccttc cgcagagatc ccaacaagct ggtgttctgt    2040
gaagttttca gtacaaccg gaagcctgca gagaccaatt taaggcactc gtgtaaacgg    2100
ataatggaca tggtgagcaa ccagcacccc tggtttggaa tggaacagga gtatactctg    2160
atgggaacag atgggcaccc tttttggttgg ccttccaatg gcttcctgg gccccaaggt    2220 ccgtattact gtggtgtggg cgcagacaaa gcctatggca gggatatcgt ggaggctcac    2280
taccgcgcct gcttgtatgc tggggtcaag attacaggaa caaatgctga ggtcatgcct    2340
gcccagtggg agttccaaat aggacccgt gaaggaatcc gcatgggaga tcatctctgg    2400
gtggcccgtt tcatcttgca tcgagtatgt gaagactttg gggtaatagc aacctttgac    2460
cccaagccca ttcctgggaa ctggaatggt gcaggctgcc ataccaactt tagcaccaag    2520
```

```
gccatgcggg aggagaatgg tctgaagcac atcgaggagg ccatcgagaa actaagcaag    2580
cggcaccggt accacattcg agcctacgat cccaaggggg gcctggacaa tgcccgtcgt    2640
ctgactgggt tccacgaaac gtccaacatc aacgactttt ctgctggtgt cgccaatcgc    2700
agtgccagca tccgcattcc ccggactgtc ggccaggaga agaaaggtta ctttgaagac    2760
cgccgcccct ctgccaactg tgaccccttt gcagtgacag aagccatcgt ccgcacatgc    2820
cttctcaatg agactggcga cgagcccttc aatacaaaaa actaaagatc cctatggcta    2880
ttggccaggt tcaatactat gtattggccc tatgccatat agtattccat atatgggttt    2940
tcctattgac gtagatagcc cctcccaatg ggcggtccca tataccatat atggggcttc    3000
ctaataccgc ccatagccac tccccccattg acgtcaatgg tctctatata tggtctttcc    3060
tattgacgtc atatgggcgg tcctattgac gtatatggcg cctcccccat tgacgtcaat    3120
tacggtaaat ggcccgcctg gctcaatgcc cattgacgtc aataggacca cccaccattg    3180
acgtcaatgg gatggctcat tgcccattca tatccgttct cacgcccct attgacgtca    3240 atgacggtaa atggcccact tggcagtaca tcaatatcta ttaatagtaa cttggcaagt    3300
acattactat tggaagtacg ccagggtaca ttggcagtac tcccattgac gtcaatggcg    3360
gtaaatggcc cgcgatggct gccaagtaca tccccattga cgtcaatggg gagggcaat    3420 gacgcaaatg ggcgttccat tgacgtaaat gggcggtagg cgtgcctaat gggaggtcta    3480
tataagcaat gctcgtttag ggaaccgcca ttctgcctgg ggacgtcgga ggagctcgaa    3540
agcttctaga caattgccgc caccatgatg tcctttgtct ctctgctcct ggttggcatc    3600
ctattccatg ccacccaggc cagtgataca ggtagacctt tcgtagagat gtacagtgaa    3660
atccccgaaa ttatacacat gactgaagga agggagctcg tcattccctg ccgggttacg    3720
tcacctaaca tcactgttac tttaaaaaag tttccacttg acactttgat ccctgatgga    3780
aaacgcataa tctgggacag tagaaagggc ttcatcatat caaatgcaac gtacaaagaa    3840
atagggcttc tgacctgtga agcaacagtc aatgggcatt tgtataagac aaactatctc    3900
acacatcgac aaaccaatac aatcatagat gtcgttctga gtccgtctca tggaattgaa    3960
ctatctgttg gagaaaagct tgtcttaaat tgtacagcaa gaactgaact aaatgtgggg    4020
attgacttca actgggaata ccccttcttcg aagcatcagc ataagaaact tgtaaaccga    4080
gacctaaaaa cccagtctgg gagtgagatg aagaagtttt tgagcacctt aactatagat    4140
ggtgtaaccc ggagtgacca aggattgtac acctgtgcag catccagtgg gctgatgacc    4200
aagaaaaaca gcacatttgt cagggtccat gaaaaagaca aaactcacac atgcccaccg    4260
tgcccagcac ctgaactcct ggggggaccc tcagtcttcc tcttccccc aaaacccaag    4320 gacaccctca tgatctcccg gaccctgag gtcacatgcg tggtggtgga cgtgagccac    4380
gaagaccctg aggtcaagtt caactggtac gtggacggcg tggaggtgca taatgccaag    4440
acaaagccac gggaggagca gtacaacagc acatatcgtg tggtcagcgt cctcaccgtc    4500
ctgcaccagg actggctgaa tggcaaggag tacaagtgca aggtctccaa caaagccctc    4560
ccagccccca tcgagaaaac catctccaaa gccaaagggc agccccgaga accacaggtg    4620
tacaccctgc ccccatcccg ggatgagctg accaagaacc aggtcagcct gacctgcctg    4680
gtcaaaggct tctatcccag cgacatcgcc gtggagtggg agagcaatgg gcagccggag    4740
aacaactaca agaccacgcc tcccgtgctg gactccgacg gctccttctt cctctacagc    4800
aagctcaccg tggacaagag caggtggcag caggggaacg tcttctcatg ctccgtgatg    4860
```

-continued

```
catgaggctc tgcacaacca ctacacgcag aagagcctct ccctgtctcc cgggaaatga    4920
tgagatctcg agttcgacat cgataatcaa cctctggatt acaaaatttg tgaaagattg    4980
actggtattc ttaactatgt tgctcctttt acgctatgtg gatacgctgc tttaatgcct    5040
ttgtatcatg ctattgcttc ccgtatggct ttcattttct cctccttgta taaatcctgg    5100
ttgctgtctc tttatgagga gttgtggccc gttgtcaggc aacgtggcgt ggtgtgcact    5160
gtgtttgctg acgcaacccc cactggttgg ggcattgcca ccacctgtca gctccttttcc   5220 gggactttcg ctttccccct ccctattgcc acggcggaac tcatcgccgc ctgccttgcc    5280
cgctgctgga caggggctcg gctgttgggc actgacaatt ccgtggtgtt gtcggggaaa    5340
tcatcgtcct ttccttggct gctcgcctgt gttgccacct ggattctgcg cgggacgtcc    5400
ttctgctacg tcccttcggc cctcaatcca gcggaccttc cttcccgcgg cctgctgccg    5460
gctctgcggc ctcttccgcg tcttcgcctt cgccctcaga cgagtcggat ctcccttttgg   5520 gccgcctccc cgcatcgatg ggggaggcta actgaaacac ggaaggagac aataccggaa    5580
ggaacccgcg ctatgacggc aataaaaaga cagaataaaa cgcacgggtg ttgggtcgtt    5640
tgttcataaa cgcggggttc ggtcccaggg ctggcactct gtcgataccc caccgagacc    5700
ccattggggc caatacgccc gcgtttcttc cttttcccca ccccaccccc caagttcggg    5760
tgaaggccca gggctcgcag ccaacgtcgg ggcggcaggc cctgccatag cggatccttt    5820
ccactgtacg cgtagcttgg cgtaatcatg gtcatagctg tttcctgtgt gaaattgtta    5880
tccgctcaca attccacaca acatacgagc cggaagcata agtgtaaag cctggggtgc     5940 ctaatgagtg agctaactca cattaattgc gttgcgctca ctgcccgctt ccagtcggg     6000 aaacctgtcg tgccagctgc attaatgaat cggccaacgc gcggggagag gcggtttgcg    6060
tattgggcgc tcttccgctt cctcgctcac tgactcgctg cgctcggtcg ttcggctgcg    6120
gcgagcggta tcagctcact caaaggcggt aatacggtta ccacagaat cagggataa     6180 cgcaggaaaa acatgtgag caaaaggcca gcaaaaggcc aggaaccgta aaaaggccgc     6240
gttgctggcg ttttttccata ggctccgccc ccctgacgag catcacaaaa atcgacgctc    6300
aagtcagagg tggcgaaacc cgacaggact ataaagatac caggcgtttc ccctggaag    6360 ctccctcgtg cgctctcctg ttccgaccct gccgcttacc ggatacctgt ccgcctttct    6420
cccttcggga agcgtggcgc tttctcatag ctcacgctgt aggtatctca gttcggtgta    6480
ggtcgttcgc tccaagctgg gctgtgtgca cgaaccccc gttcagcccg accgctgcgc     6540
cttatccggt aactatcgtc ttgagtccaa cccggtaaga cacgacttat cgccactggc    6600
agcagccact ggtaacagga ttagcagagc gaggtatgta ggcggtgcta cagagttctt    6660
gaagtggtgg cctaactacg gctacactag aagaacagta tttggtatct gcgctctgct    6720
gaagccagtt accttcggaa aaagagttgg tagctcttga tccggcaaac aaaccaccgc    6780
tggtagcggt ggtttttttg tttgcaagca gcagattacg cgcagaaaaa aaggatctca    6840
agaagatcct ttgatctttt ctacggggtc tgacgctcag tggaacgaaa actcacgtta    6900
agggattttg gtcatgagat tatcaaaaag gatcttcacc tagatccttt taaattaaaa    6960
atgaagtttt aaatcaatct aaagtatata tgagtaaact tggtctgaca gttaccaatg    7020
cttaatcagt gaggcaccta tctcagcgat ctgtctattt cgttcatcca tagttgcctg    7080
actccccgtc gtgtagataa ctacgatacg ggagggctta ccatctggcc ccagtgctgc    7140
aatgataccg cgagacccac gctcaccggc tccagattta tcagcaataa accagccagc    7200
cggaagggcc gagcgcagaa gtggtcctgc aactttatcc gcctccatcc agtctattaa    7260
```

```
ttgttgccgg gaagctagag taagtagttc gccagttaat agtttgcgca acgttgttgc    7320
cattgctaca ggcatcgtgg tgtcacgctc gtcgtttggt atggcttcat tcagctccgg    7380
ttcccaacga tcaaggcgag ttacatgatc ccccatgttg tgcaaaaaag cggttagctc    7440
cttcggtcct ccgatcgttg tcagaagtaa gttggccgca gtgttatcac tcatggttat    7500
ggcagcactg cataattctc ttactgtcat gccatccgta agatgctttt ctgtgactgg    7560
tgagtactca accaagtcat tctgagaata gtgtatgcgg cgaccgagtt gctcttgccc    7620
ggcgtcaata cgggataata ccgcgccaca tagcagaact ttaaaagtgc tcatcattgg    7680
aaaacgttct cggggcgaa  aactctcaag gatcttaccg ctgttgagat ccagttcgat    7740
gtaacccact cgtgcaccca actgatcttc agcatctttt actttcacca gcgtttctgg    7800
gtgagcaaaa acaggaaggc aaaatgccgc aaaaaaggga ataagggcga cacggaaatg    7860
ttgaatactc atactcttcc tttttcaata ttattgaagc atttatcagg gttattgtct    7920
catgagcgga tacatatttg aatgtattta gaaaaataaa caaatagggg ttccgcgcac    7980
atttccccga aaagtgccac ctgacgtcta agaaaccatt attatcatga cattaaccta    8040
taaaaatagg cgtatcacga ggccctttcg tc                                  8072
```